(12) United States Patent
Rouviere

(10) Patent No.: US 6,329,151 B1
(45) Date of Patent: Dec. 11, 2001

(54) HIGH DENSITY SAMPLING OF DIFFERENTIALLY EXPRESSED PROKARYOTIC MRNA

(75) Inventor: Pierre E. Rouviere, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/655,270

(22) Filed: Sep. 5, 2000

Related U.S. Application Data

(60) Provisional application No. 60/152,542, filed on Sep. 3, 1999.

(51) Int. Cl.⁷ ............................... C12Q 1/68; C12P 19/34
(52) U.S. Cl. .............................................. 435/6; 435/91.2
(58) Field of Search ........................................ 435/6, 91.2

(56) References Cited

U.S. PATENT DOCUMENTS 6,156,502 * 12/2000 Beattie ..................................... 435/6

FOREIGN PATENT DOCUMENTS

WO87.48342    11/1998  (WO).

OTHER PUBLICATIONS

Froussard: Nucleic Acid Research, GB, Oxford University Press, vol. 20, No. 11, 1992—P. 2900.
Zhao et al.: Biotechniques, US, Eaton Publishing, Natick, vol. 24, No. 5, May 1998—pp. 842–852.
K Kwok Wong et al., Proceedings of the National Academy of Science of USA, Washington, U.S. vol. 91, Jan. 1994–pp. 639–643.
Rivera–Marrero Carlos A. et al., Microbial Pathogenesis, vol. 25, No. 6, Dec. 1998—pp. 307–316.
Kwaik Y A et al.: Molecular Microbiology, Blackwell Scientific, Oxford, GB, vol. 21, No. 3, 1996, pp. 543–546.
Database Geneseq Online ID/AC Q39044, Mar. 1993—XP002156289—Abstract.
Telenius H et al: Genomics, US, Academic Press, San Diego, vol. 13, 1992, pp. 718–725.
Welsh J et al: Nucleic Acids Research, GB, Oxford University Press, Surrey, vol. 18, No. 24, Dec. 25 1990—pp. 7213–7218.
Rindi Laura et al: Biochemical and Biophysical Research Communications, vol. 258, No. 1, Apr. 29, 19999–pp. 94–101.
Brzostowicz Patricia C et al: Journal of Bacteriology, vol. 182, No. 15, Aug. 2000—pp. 4241–4248.
Chuang et al., J. Bacteriol. 175: 5242–5252 (1993).
Duggan et al., Nat. Genet. 21:10–14 (1999).
Rafalski et al., Acta Biochimica Polonica 45:929–934 (1998).
Liang et al., Science 257:967–971 (1992).
Liang et al., Nucleic Acids Res. 21: 3269–3275 (1993).
Williams et al., Nucleic Acids Res. 18:6531–6535 (1990).
Welsh et al., Nucleic Acids Res. 20:4965–4970 (1992).
Abu Kwaik et al., Mol. Microbiol. 21:543–556 (1996).
Fleming et al., Appl. Environ. Microbiol. 64:3698–3706 (1998).
Wong et al., Proc. Natl. Acad. Sci. USA 91: 639–643 (1994).
Yuk et al., Mol. Microbiol. 28:945–959 (1998).
Zhang et al., Science 273: 1234–1236 (1996).

* cited by examiner

*Primary Examiner*—Kenneth R. Horlick
*Assistant Examiner*—Teresa Strzelecka

(57) ABSTRACT

A reliable and rapid method to identify differentially expressed genes in microbes has been developed. The method relies on the use of a large number of arbitrarily primed PCR reactions. The method has been used to identify the DNA sequences of genes involved in the degradation of the picric acid from *Rhodococcus erythropolis* strain HL PM-1, and genes involved in cyclohexanol degradation from a consortium of organisms.

26 Claims, 9 Drawing Sheets

Figure 1:
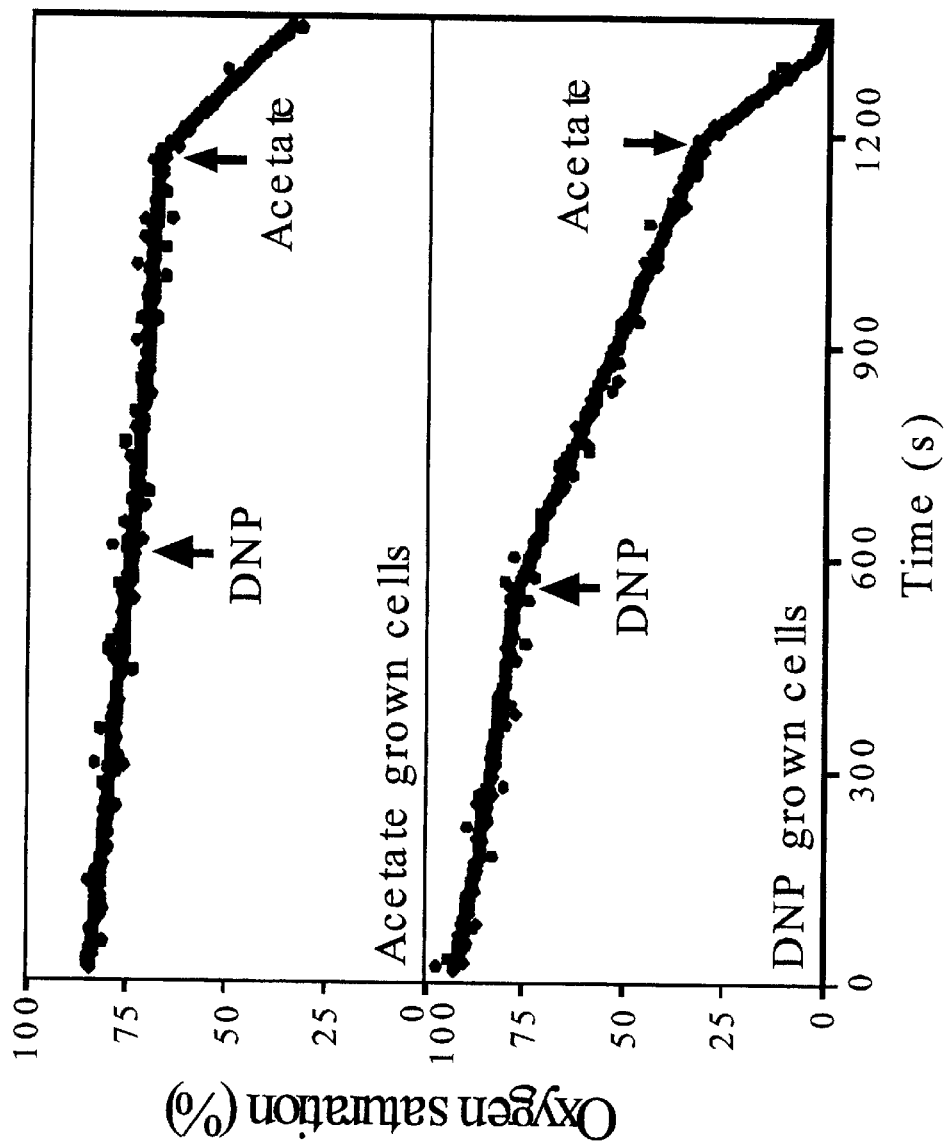

ORF 1  Transcription Factor
ORF 2  Dehydratase
ORF 3  F420-dpdt Dehydrogenase #1
ORF 4  Aldehyde Dehydrogenase
ORF 5  Acyl CoA Synthase ORF 6   Transcription Regulator
ORF 7   F420/NADPH oxidoreductase
ORF 8   F420-dpdt Dehydrogenase #2
ORF 9   Enoyl-CoA Hydratase
ORF 10  Acyl-CoA Dehydrogenase

SEQUENCE LISTING

<160> NUMBER OF SEQ ID NOS: 37

<210> SEQ ID NO 1
<211> LENGTH: 12508
<212> TYPE: DNA
<213> ORGANISM: Rhodococcus erythropolis HL PM-1

<400> SEQUENCE: 1

```
cgcctgaccg accgcttcac cctgctgacc cgcggcaacc ggggtgcgcc gacgcggcag      60
cagaccctgc ggttgtgtat cgactggagc ttcgagttgt gcaccgccgg tgagcaactg     120
gtgtggggc gggtggcggt cttcgcgggg tgcttcgaac tcgatgccgc ggagcaggtg     180
tgtggcgagg gcctggcctc gggcgagtta ttggacacgc tgacctccct ggtgagaaag     240
tcgatcctga tccgggagga atccgggtcg gtggtgcttt tccggatgct cgagactctc     300
cgtgagtacg gctacgagaa gctcgagcag tccggcgagg cattggatct gcgtcgccgg     360
caccggaatt ggtacgaggc gttggcgctg gatgcggaag ccgagtggat cagcgcgcgc     420
caactcgact ggatcacccg gctgaagcgg gaacaaccga atctgcggga ggccctcgaa     480
ttcggcgtcg acgacgatcc cgtcgccggt ctgcgcaccg ccgccgcact gttcctgttc     540
tgggctctc agggcctcta caacgagggg cggcgctggc tcggccagct gctcgcccgc     600
cagagcggcc caccgacggt cgagtgggtc aaggccctcg aacgcgccgg catgatggcc     660
aatgtgcagg gtgatctgac tgccggagcc gcactcgtgg cggagggggcg agcgctcact     720
gcccacacga gtgaccccat gatgcgggct ctcgttgcat acggcgatgg catgcttgcc     780
ctctacagcg gtgatctggc gcgtgcgtct tcggacctcg aaaccgctct gacggagttc     840
accgcgcgcg gtgaccgaac gctcgaagta gccgcactgt accgtttggg gttggcgtac     900
ggactgcgcg gctcgacgga ccggtcgatc gaacgtctcg agcgcgttct cgcgatcacg     960
gagcagcacg gcgagaaaat gtatcggtcg cactcgttgt gggctctggg tatcgccctg    1020
tggcggcacg gggacggcga tcgcgcggtc cgcgtgctcg agcagtcgct ggaggtgacc    1080
```

```
cggcaagtgc acggcccacg tgtcgccgcg tcctgtctcg aggcactggc ctggatagcc      1140
tgcggaatgc gtgacgaacc gagggctgcg gttctgttgg gagccgcaga agagttggcg      1200
cgatcagtgg gcagtgccgt ggtgatctac tccgatcttc ttgtctacca tcaggaatgc      1260
gaacagaagt ctcgacggga actcggggac aaaggattcg cggcggccta ccgcaagggt      1320
cagggactcg gtttcgacgc ggccatcgcc tatgccctcc gcgagcaacc gccgagcacc      1380
tccggaccca ccgccggtgg gtcgacgcga ctgaccaagc gggaacgcca agtcgccggc      1440
ctcatcgccg aaggtctcac caaccaggcc atcgccgacc gcctggtgat ctctccacgg      1500
accgcgcaag ggcacgtgga gcacatcctg gccaagctgg gtttcacgtc ccgggcgcag      1560
gtcgcggcct gggtcgtcga gcggaccgac gactgaatgg aacacctccg ctcgcgttga      1620
acgcggcagt cggtgacgac cgcgaccgcg ggtcggtccc tggaatcgcg acgtaaacgg      1680
ttctccccga acatatgtgg cctttcgttt cgcgttgctg cgcgcccgcc atttcccgtc      1740
gtgggaccga atcgcccgcc acgcaccggc cgccggaaat ctgctccctc ttgacagcgg      1800
gcggtggtgc tcgtaacgtc cgtggagttc caaataatga tgtcagttca gcatagtgaa      1860
cggagcttgt gatggggttc accggaaatg tcgaggcgct gtcgggaatc cgagtggtcg      1920
acgccgcgac gatggtcgcc ggcccttgg gtgcgtcgct gctcgccgat ttcggtgccg      1980
acgtcatcaa ggtcgagccg atcggcggcg acgagtcgcg gacgttcggg ccgggacgag      2040
acggcatgag tggtgtctat tccgcgtga accgaaacaa gcgcgccctc gcgctcgacc      2100
ttcggacgga ggcgggccgt gacctgttcc acgagctgtg ctcgacagcg acgtgctca      2160 tcgagaacat gctgccggcg gtacgggaac gattcgggct gactgccgcc gagcttcgcg      2220
aacggcaccc tcacctgatc tgcctcaatg tcagcgggta cggcgagacc ggcccctcg      2280 cgggtcgccc cgcaatggac ccggtggctc aggcgctcac cggactcatg caggcgaccg      2340
gtgagcgctc ggggaggtcg ctcaaggccg gtccgcccgt cgccgacagt gcggcgggct      2400
acctggtcgc gatcgccgcc ctcgtcgcgc tcttcgcgaa acagcgcacg ggggaggggc      2460
aaagtggctc ggtgtccctg gtgggggcgc tgttccattt gcagacgccg tggctggggc      2520
agtacctcct ggccgactac atccagggca aggtgggcaa cggcagcaat ttctacgcgc      2580
cgtacaacgc ctatacgacc cgtgacggcg gcgcggtgca tgtcgttgcc ttcaacgacc      2640
gccacttcgt caagctcgcc cgggcgatgg gtgccgaggc tctgatcgac gatccgcgct      2700
tcgcgcaggc cgcatcccga ctggagaacc gtgaggccct cgacgacgcc gtcgcaccct      2760
ggttcgccga ccgcgaccgg gacgacgtgg ttgcactgct ctcggcccac gacatcatct      2820 gtgcccccgat tctcgcgtac gacgaggccg tcaggcatcc ccagatccag gcactggacc      2880
tcgtcgtcga catcacccac gacgaactcg gaccgctgca ggttccgggt ctcccggtca      2940
agctctcggg caccccggga cacgtacacc gcccaccgac gtcgttgggc gagcacacca      3000
ccgagattct cagcgatctc ggctacaagg acgaccggat tgcggccctc cgggccgaac      3060
gggtcgtccg atgaccacag aacatggcga aggaaccac caatgaaggt cggaatcagg      3120
atcccgggag caggaccgtg ggcagggccc gaggcgatca cggaggtgtc gcggttcgct      3180
gagaagatcg gcttcgactc gctctggatg actgatcatg tggccttgcc gacccgagtc      3240
gagacggcgt acccgtacac cgacgacggc aagttcctgt gggatccggc cacgccgtac      3300
ctcgactgcc tcacgtcgtt gacgtgggcg cggccgcga ccgagcggat ggagctcggc      3360
acgtcgtgcc tcatcctgcc gtggcgtccg ctcgtccaga ccgccaagac actggtgagc      3420
```

-continued

```
atcgacgtga tgtcgcgcgg ccggctgtcg gtcgccatcg gcgtgggctg gatgaaggag   3480
cagttcgagc tgctgggagc gcctttcaag gaccggggga agcggaccac ggagatggtc   3540
aacgcgatgc ggcacatgtg gaaggaagac gaggtcgcct tcgacggtga gttctaccaa   3600
ctccacgact tcaagatgta tccgaagccg gtgcggggca cgatccccgt ctggttcgcg   3660
ggatacagca ccgcctccct gcgccgtatc gccgccatcg gcgacgggtg caccccattg   3720
gcgatcgggc cggaggagta cgccggctac ctggccaccc tgaagcaata cgccgaggaa   3780
gccggccgcg acatgaacga aatcaccctc accgcgcggc tctgcggaa ggcgccgtac    3840
aacgccgaga cgatcgaagc gtacggcgaa ctcggtgtca cccacttcat ctgcgacacg   3900
tcgttcgagc acgacaccct cgaagcaacc atggacgagc tcgccgagct tgccgacgcc   3960
gtcctcccca ccgcacacaa cctgccctga cggcccggcg gaagaaagga cgagaattgt   4020
gcaggcactc acctcatcgg ttcccctcgt catcggcgac caactgaccc catcgtcgac   4080
gggggcgacc ttcgactcga tcaacccggc cgacgggtcg cacctggcca gcgtcgccga   4140
ggccacggcc gcggacgtcg cgcgtgcggt cgaagccgcg aaggcggcgg ccaggacgtg   4200
gcagcgcatg cgcccggccc agcgaacccg cctgatgttc cgctacgccg cgctgatcga   4260
ggaacacaag accgagctcg cccagctgca gagtcgggac atgggcaagc ccatccgcga   4320
gtcgctcggg atcgacctgc cgatcatgat cgagacgctc gagtacttcg cgggcctcgt   4380
gaccaagatc gagggccgaa cgacgccggc gcccggccgt ttcctcaact acaccctgcg   4440
tgagccgatc ggtgtggtgg gcgccatcac tccctggaat tttcctgcag tgcaggcggt   4500
ctggaagatc gccccggctc ttgcgatggg caacgccatc gtgctgaagc ctgcgcagct   4560
cgcaccactc gtgcccgtgg cactcggcga gctcgccctc gaggcgggtc tgccgcccgg   4620
gctggtcaac gtcctgcccg ccgcgggtc ggtagcgggt aacgccttgg tgcagcaccc    4680
atcggtcggc aaggtgacgt tcaccggctc gaccgaggtc ggccagcaga tcggccggat   4740
ggcggccgac cgcctcatca cggcttcgct ggagctgggc ggaaagtctg cgctcgtggc   4800
gttcggcgac tcgtccccga aggcggtcgc agccgtggtc ttccaggcga tgtacagcaa   4860
ccagggtgag acctgcacgg cgccgagcag gttgctcgtc gagcggccga tctacgacga   4920
ggtggtcgag ctcgtccagg cacgtgtcga ggccgcccgg gtgggcgacc cgctcgaccc   4980
cgacacggag atcggcccgt tgatcagtgc cgagcagcgg gagtcggtcc actcgtacgt   5040
cgtctccggg accgaggaag cgccacgct gatcagcggt ggcgaccagt cgccgaccgg    5100
agcgccggag cagggattct actaccgtcc gacgctcttc tccggagtca ccgcggacat   5160
gcgcatcgct cgggaggaga tcttcggacc cgtgctgtcg gtgctgccgt tcgagggaga   5220
agaggaggcg atcaccctgg ccaacgacac cgtcttcggg ctggccgcgg gcgtcttcac   5280
ccgcgatgtg ggccgcgcac tgcggttcgc gcagacgctc gacgccggca acgtgtggat   5340
caacagctgg ggagtgctca acccggcgtc gccgtatcga ggcttcgggc agagcggcta   5400
cggcagcgac ctcggccagg cggccatcga aagcttcacc aaggagaaga gcatatgggc   5460
acgcctggac tgacctccgg gacatcgagg tcacggacca tcaggcggtt gatcgacgcc   5520
cgccacaccc aggattggaa gccagcggcg gactacacga tcaccgagga cgccctcttc   5580
tcacgcgacc ccgacgccgt ggccgtgctg cgcggggggc tccacacgcc cgagaaggtg   5640
acgttcggtc aggtacagca cgccgctgtg cgcgtcgccg tgtcctccg gtcccgcggg    5700
gtcgagcccg gtgaccgcgt ggtcctgtac ctcgacccct cggtggaggc cgccgaggtc   5760
gtcttcgggg tgctcgtcgc cggcgccgtg ctcgtgcccg tccgcgact gctcaccggt    5820
```

-continued

```
acctcggtgg cgcaccggct cgccgactcg ggcgcgactg tgctggtcac ggacggtccg      5880
ggcgtcgacc ggctggagtc gacaggatgt tccctgcacg acgtcgacgt gctcacggtg      5940
gacggcgccc acggcgcgcc gctcggggac ctgacccgcc gggtcgaccc gctcgccccg      6000
gtgccgcggc ggtcctcgga tcttgctctg ctgatgtaca cgtcgggcac cagcggcccg      6060
cccaagggca tcgttcacgg ccatcgggtc ctgctcggac atgcgggggt cgactacgcc      6120
ttcgaactgt tcaggccggg tgacgtctat ttcggcactg cggactgggg gtggatcggc      6180
ggcctgatgc tcgggttgct ggttccgtgg tctctcggg ttcctgtcgt ggctcaccgg      6240
ccgcagcgtt tcgatcccgg cgccaccctg gacatgctga gccggtacag cgtgacgacc      6300
gccttcctgc cggcgtcggt tcttcggatg tttgccgaac acggggaacc ggcccagcgg      6360
cgtctgcggg cggtggtgac cggaggcgag cccgccggcg cggtggaact cggctgggcc      6420
cggcggcatc tcagcgacgc cgtcaacaag gcctacggtc agaccgaggc caacgcgctc      6480
atcggcgact ccgctgttct cggatccgtc gacgacgcga ccatgggcgc tccgtatccc      6540
gggcaccgca tcgcgctcct ggacgacgcg ggcactcacg tcgcgcccgg tgaggtcggt      6600
gagattgcgc tggaacttcc ggattcggtt gcgctgctcg gctattggga tgcgtcgtcg      6660
gctagtgtga tacctcccgc cgggagttgg caccggacag gcgacctggc acggctcgca      6720
catggacgcc ggctggagta cctcggccgc gccgacgacg tgatcaagag ccgcggctac      6780
cgcatcggtc cggcggagat cgaagaggca ctgaagcgtc accccaggt cctggacgcg      6840 gcggcggtag ggctgcccga cccggagtcg gggcagcagg tcaaggcatt cgtccacctc      6900
gctgccggca aactcaccga ggagatttcg gcggaactcc gtgaactcgt cgccgccgcg      6960
gtcggcccac acgcacgccc ccgcgagata gaggcagtcg cagcgttgcc gcgcacggag      7020
accggaaagg tccggcggcg ggaactggtg ccgccctcgg cttagcattc ggcgactgcc      7080
gcggcctcgt ggagcgccat ccacccaccc gaacacagaa gtgcaagaag aaggacgaag      7140
caatgcgaaa gttctggcac gtcggcatca atgtgaccga catggacaaa tcgatcgact      7200
tctatcggcg aatcggtttc gaggtagtgc aggatcggga ggtggaggac agcaaccttg      7260
cgcgggcatt catggtcgag ggtgccagca agctccgctt cgcacacttg cgcctgaacg      7320
actccccgga cgaggcgatg ctggacctca tcgagtggag ggacgcacgt tccgagggggc      7380 gagcgcagag cgacctcgtg cacccgggac tctgccgatt ctcgatcctc accgacgaca      7440
tcgacgccga gtatgcacgg ctggcggacg acggcgtcca gttcctgcac gcgccgcaga      7500
cgatcatggg tccggacggc gtcaagggct ggcggctgct cttcgcgcgc gatcccgacg      7560
gcacgctgtt ccatttcgcc gaacttgtgg ggcaggccgc tacggtcagc tgacagcatt      7620
cgcacgacga aggtaggaac ccttgaccaa ggcagaagtc ccgggaagca gcgcgactga      7680
cgagcggggc gagcaatcca gcgagcagct ggtgcccgca atctcgcgcg caacccgcgt      7740
actcgagaca ctggtccagc agtccaccgg agccacactc accgagttgg ccaagcggtg      7800
cgctctggcg aagagcacgg catcggtcct gctccgacc atggtggtcg agggcctcgt      7860
cgtgtacgac caggagacgc gccggtacaa cctcggcccg ctgctcgtgg agttcggcgt      7920
ggctgcgatc gcgcgaacat cggcggtcgc cgcgtcgcgg acgtacatgg agtggttggc      7980
cgagcggacc gagctggcat gtctcgccat ccagccgatg ccggacggtc acttcacggc      8040
gatcgcgaag atcgagagcc gcaaggccgt caaggtcacc atcgaggtcg gctctcgctt      8100
cggtcgagac actccgttga tcagccgact cgcggcggca tggccgagca gggtcgccc      8160
```

```
ggagcttgtc gagtacccg ccgatgagct cgacgagctc cgggcgcagg gctacggcgc    8220
tgtctatggc gaatatcgac cggaactcaa cgtcgtgggg gtcccggtgt cgaccgaga    8280
cggcgagccg tgtctgttca tcgccctgct cggtatcggc gacgatctca cagccgacgg    8340
tgtggccggg atcgccgact acctcgtcac ggtttcgcgg gagatcagct cgcatatcgg    8400
cggccgcatt ccggcggact acccgactcc tgtcggggcc cccgacctcg cgccggggcg    8460
cggctgaccg agcccccgat ttcaatcaag cggcggcccc accggggcct gccgctccga    8520
gtcgaccccc aacggtcggc tgaccacctc cggtgcaacg cgtcggaggt gtcccgtccc    8580
aatgtgtagg agacagacat gaagagcagc aagatcgccg tcgtcggcgg caccggaccc    8640
cagggaaagg ggctggccta ccggttcgcg gcggccggct ggcctgtcgt catcggatcg    8700
cgttctgccg aacgcgcgga ggaggcggcc ctcgaggtgc gcagacgcgc cggtgacggc    8760
gccgtggtca gcgccgccga caatgcgtcg gcagctgccg actgtcccat catcctgctg    8820
gtcgtcccat acgacggcca tcgtgagctg gtttcggaac tggcacccat cttcgcgggc    8880
aagctcgtcg tcagctgcgt gaatccgctc ggcttcgaca agtccgggc ctacggtttg    8940
gacgtcgagg aagggagcgc cgccgagcaa ctgcgcgacc tcgtgcccgg tgccacggtg    9000
gtcgctgcct ttcaccatct gtcggcggtc aacctctggg aacatgaggg ccccttccc    9060
gaggatgtgc tcgtgtgcgg cgacgatcgg tccgcgaagg acgaggtggc tcggctcgca    9120
gtcgcgatca ccggccggcc gggcatcgac ggaggggcgc tgcgggtggc gcggcagctc    9180
gaaccgttga ccgccgttct catcaatgtc aaccggcgct acaagacgct ctccggtctc    9240
gccgtgaacg gggttgttca tgatccacga gctgcgtgag taccttgcgc tgccgggccg    9300
tgccgaggac ctgcaccgca ggttcgccga cgacacgctg gccctgttcg cggaattcgg    9360
gctgcaggtc gagggcttct ggcacgaggc aggcaaccgt gcccggatcg tgtacctgtt    9420
ggcgttcccc gacttcgagg ccgcggacgc gcattgggcc cggttccagg ccgacccccg    9480
gtggtgtgcg ttgaaggcac gcaccgagag cgacgggccg ctcatctcgg agatccggag    9540
cacgttcctg atcaccccgt catacgcccg ctcctgagcg gcaccgaacg aggctggact    9600
gactcttgac cgtcgccgtg ttctgccctt aacctgttcc atatagtgat cgagttcaa    9660
catcatgaag agaagttcga tgatcaaagg catccagctc catggttggg ctgacgggcc    9720
gcagatggtc gaagtggccg agatcgccgc tgggagtttc gaaaccgtct ggctcagtga    9780
ccaactccag tccgaggcg tcgccgttct cctcggcgca atcgctgcgc gcaccggtgt    9840
cggagtcggc actgcagtga cctttccctt cgggcggaac cccctcgaga tggcatccag    9900
catggccacc ctggcggagt tcatgcccga aggacgtcgg gtcaccatgg aatcggcac    9960
cggaggtggg ctggtgagtg cgctcatgcc gctgcagaac ccgatcgacc gcgtggccga   10020
gttcatcgcg atgtgccggc ttctctggca gggcgaagcg atccgaatgg gtgactaccc   10080
acagatctgt accgccctcg gcttgcgtga ggatgctcgg gcgtcgttct cctggacgag   10140
caagcccgac gtgcgcgtcg tcgtcgccgg cgccggaccg aaagtgctgg agatggccgg   10200
cgaactcgca gacggcgtca tctgcgccag caatttcccg gcccacagcc tcgcggcctt   10260
ccgtagcggc cagttcgacg cggtgagcaa cctcgatgcg ctcgaccggg ccgaaagcg   10320
cagtcggcgg ggggagttca cccggatcta cggcgtgaac ctgtccgtgt ctgccgaccg   10380
ggagagtgcc tgcgcggccg cgcggcgaca ggcgacactc attgtgagcc aacagcctcc   10440
agagaatctg caccgggtcg gctttgagcc ctccgactac gccgccaccc gagcggcgct   10500
caaagccgga gacggcgtag acgcagccgc cgacctcctc ccacaggaag tcgcggacca   10560
```

-continued

```
actcgtggtc tcgggcacgc ccggcgactg catcgaggcg ctggccgagc tgctcgggta    10620
cgcggaggat gccggattca ccgaggccta catcggtgcc ccggtcggcc cggacccacg    10680
cgaggcggtc gagctcctca cgtcccaggt cctgccggag ctcgcatgag cgccggcacg    10740
caggcaaccc gggacctgtg cccggccgaa caccacgacg gtctggtcgt cctgacgctc    10800
aatcgtcccg aggcgcgcaa cgccctcgac gtacccctgc tcgaggcgtt cgccgctcgg    10860
cttgccgagg gaaaacgcgc gggcgccggc gtcgtcctcg tgcgcgcgga agggccggcg    10920
ttctgcgcag gagccgatgt gcgttccgac gacggcacgg cgaccggccg accgggcctc    10980
cggcgccgtc tcatcgagga gagcctcgac ctgctgggcg actaccggc ggcggtggtc    11040 gcggtgcagg gcgccgcgat cggcgccggg tgggcaatag ccgcggcagc ggacatcacg    11100
ctggcctcgc ctaccgcttc gttccgattt cccgagctcc cactcggatt cccgccccct    11160
gacagcacgg tgcgcatact cgaagccgcc gtcgcccgg cgcgggcgct gcggctcctg    11220
gccctgaacg agcgcttcgt cgccgacgac ctggccaggc tcggtctggt ggacgtcgtt    11280
cccgaggatt cgctcgacgt gacggcgcgc gagacggccg cccgactcgc ggttcttccc    11340
ctcgagttgc tgcgcgatct caaaacaggc ctctccgccg ggaagcggcc cccctccatc    11400
gaccgaccag cctcgaaagg cagtcatgag cactagcatt cacattcaga ccgacgagca    11460
ggcgcacctc cgcaccactg cccgggcatt cctggccaga cacgctcccg cgctcgacgt    11520
gcgcatctgg gacgaggcgg ggaaataccc cgagcacctg ttccgcgaga tcgcccgcct    11580
cgggtggtac gacgtggtgg ccggagacga ggtcgtcgac ggtacggccg gcctgctgat    11640
cacgctctgc gaagagatcg gccgggcgag ttcggacctc gtggccttgt tcaacctgaa    11700
cctcagtggg ctgcgcgaca tccaccgctg gggcacgccc gaacagcagg agacgtacgg    11760
tgcaccggtg ctggccggcg aggcgcgcct gtcgatcgcg gtgagcgaac ccgacgtggg    11820
ctcggacgcc gcgagcgtgg ccacgcgcgc cgagaaggtc ggggactcgt ggatcctcaa    11880
cggccagaag acctactgcg agggcgcggg actaaccggc gcagtaatgg aactcgtcgc    11940
ccgagtggga gggggtggtc gcaagcgcga ccaactcgcc atatttctgg tgccggtcga    12000
tcatccgggg gtcgaggtcc gccgcatgcc cgcgctcggc cggaacatca gcggcatcta    12060
cgaggtcttc ctgcgggacg ttgcgcttcc ggcgacggc gtgctgggtg agcccggtga    12120
aggatggcag atcctcaagg aacgtctggt gctcgagcgg atcatgatca gttccggctt    12180
cctcggcagc gtcgccgcgg tactcgacct gacggtccac tacgccaacg agcgcgagca    12240
gttcggcaag gcactctcga gctatcaggg cgtgaccttg ccctcgccg agatgttcgt    12300 caggctcgac gcggcccagt gcgcggtacg ccgttcggcc gacctcttcg acgcgggtct    12360
gccgtgcgag gtggagagca cgatggcgaa gttcctctcc ggccagctct acgcggaggc    12420
ctctgctctg gcgatgcaga ttcagggcgc ctacggctat gtgcgcgacc atgccttgcc    12480
gatgcaccac tccgacggga tccccggg                                      12508
```

<210> SEQ ID NO 2
<211> LENGTH: 1596
<212> TYPE: DNA
<213> ORGANISM: Rhodococcus erythropolis HL PM-1

<400> SEQUENCE: 2

```
cgcctgaccg accgcttcac cctgctgacc gcggcaacc ggggtgcgcc gacgcggcag      60
cagaccctgc ggttgtgtat cgactggagc ttcgagttgt gcaccgccgg tgagcaactg    120
```

-continued

```
gtgtggggc gggtggcggt cttcgcgggg tgcttcgaac tcgatgccgc ggagcaggtg    180
tgtggcgagg gcctggcctc gggcgagtta ttggacacgc tgacctccct ggtggagaag    240
tcgatcctga tccgggagga atccggtcg gtggtgcttt ccggatgct cgagactctc     300 cgtgagtacg gctacgagaa gctcgagcag tccggcgagg cattggatct gcgtcgccgg    360
caccggaatt ggtacgaggc gttggcgctg atgcggaag ccgagtggat cagcgcgcgc    420
caactcgact ggatcacccg gctgaagcgg gaacaaccga atctgcggga ggccctcgaa    480
ttcggcgtcg acgacgatcc cgtcgccggt ctgcgcaccg ccgccgcact gttcctgttc     540
tgggcctctc agggcctcta caacgagggg cggcgctggc tcggccagct gctcgcccgc    600
cagagcggcc caccgacggt cgagtgggtc aaggccctcg aacgcgccgg catgatggcc    660
aatgtgcagg gtgatctgac tgccggagcc gcactcgtgg cggaggggcg agcgctcact    720
gcccacacga gtgaccccat gatgcgggct ctcgttgcat acggcgatgg catgcttgcc    780
ctctacagcg gtgatctggc gcgtgcgtct tcggacctcg aaaccgctct gacggagttc    840
accgcgcgcg gtgaccgaac gctcgaagta gccgcactgt acccgttggg gttggcgtac    900
ggactgcgcg gctcgacgga ccggtcgatc gaacgtctcg agcgcgttct cgcgatcacg    960
gagcagcacg gcgagaaaat gtatcggtcg cactcgttgt gggctctggg tatcgccctg    1020
tggcggcacg gggacggcga tcgcgcggtc cgcgtgctcg agcagtcgct ggaggtgacc    1080
cggcaagtgc acggcccacg tgtcgccgcg tcctgtctcg aggcactggc ctggatagcc    1140
tgcggaatgc gtgacgaacc gagggctgcg gttctgttgg gagccgcaga agagttggcg    1200
cgatcagtgg gcagtgccgt ggtgatctac tccgatcttc ttgtctacca tcaggaatgc    1260
gaacagaagt ctcgacggga actcggggac aaaggattcg cggcggccta ccgcaagggt    1320
cagggactcg gtttcgacgc ggccatcgcc tatgccctcc gcgagcaacc gccgagcacc    1380
tccgacccca ccgccggtgg gtcgacgcga ctgaccaagc gggaacgcca agtcgccggc    1440
ctcatcgccg aaggtctcac caaccaggcc atcgccgacc gcctggtgat ctctccacgg    1500
accgcgcaag gcacgtggga gcacatcctg gccaagctgg gtttcacgtc ccgggcgcag    1560
gtcgcggcct gggtcgtcga gcggaccgac gactga                             1596
```

<210> SEQ ID NO 3
<211> LENGTH: 532
<212> TYPE: PRT
<213> ORGANISM: Rhodococcus erythropolis HL PM-1

<400> SEQUENCE: 3

```
Arg Leu Thr Asp Arg Phe Thr Leu Leu Thr Arg Gly Asn Arg Gly Ala
  1               5                  10                  15

Pro Thr Arg Gln Gln Thr Leu Arg Leu Cys Ile Asp Trp Ser Phe Glu
             20                  25                  30

Leu Cys Thr Ala Gly Glu Gln Leu Val Trp Gly Arg Val Ala Val Phe
         35                  40                  45

Ala Gly Cys Phe Glu Leu Asp Ala Ala Glu Gln Val Cys Gly Glu Gly
     50                  55                  60

Leu Ala Ser Gly Glu Leu Leu Asp Thr Leu Thr Ser Leu Val Glu Lys
 65                  70                  75                  80

Ser Ile Leu Ile Arg Glu Glu Ser Gly Ser Val Val Leu Phe Arg Met
                 85                  90                  95

Leu Glu Thr Leu Arg Glu Tyr Gly Tyr Glu Lys Leu Glu Gln Ser Gly
            100                 105                 110
```

```
Glu Ala Leu Asp Leu Arg Arg Arg His Arg Asn Trp Tyr Glu Ala Leu
        115                 120                 125
Ala Leu Asp Ala Glu Ala Glu Trp Ile Ser Ala Arg Gln Leu Asp Trp
        130                 135                 140
Ile Thr Arg Leu Lys Arg Glu Gln Pro Asn Leu Arg Glu Ala Leu Glu
145                 150                 155                 160
Phe Gly Val Asp Asp Pro Val Ala Gly Leu Arg Thr Ala Ala Ala
                    165                 170                 175
Leu Phe Leu Phe Trp Gly Ser Gln Gly Leu Tyr Asn Glu Gly Arg Arg
            180                 185                 190
Trp Leu Gly Gln Leu Leu Ala Arg Gln Ser Gly Pro Pro Thr Val Glu
        195                 200                 205
Trp Val Lys Ala Leu Glu Arg Ala Gly Met Met Ala Asn Val Gln Gly
        210                 215                 220
Asp Leu Thr Ala Gly Ala Ala Leu Val Ala Glu Gly Arg Ala Leu Thr
225                 230                 235                 240
Ala His Thr Ser Asp Pro Met Met Arg Ala Leu Val Ala Tyr Gly Asp
                    245                 250                 255
Gly Met Leu Ala Leu Tyr Ser Gly Asp Leu Ala Arg Ala Ser Ser Asp
            260                 265                 270
Leu Glu Thr Ala Leu Thr Glu Phe Thr Ala Arg Gly Asp Arg Thr Leu
        275                 280                 285
Glu Val Ala Ala Leu Tyr Pro Leu Gly Leu Ala Tyr Gly Leu Arg Gly
        290                 295                 300
Ser Thr Asp Arg Ser Ile Glu Arg Leu Glu Arg Val Leu Ala Ile Thr
305                 310                 315                 320
Glu Gln His Gly Glu Lys Met Tyr Arg Ser His Ser Leu Trp Ala Leu
                    325                 330                 335
Gly Ile Ala Leu Trp Arg His Gly Asp Gly Asp Arg Ala Val Arg Val
            340                 345                 350
Leu Glu Gln Ser Leu Glu Val Thr Arg Gln Val His Gly Pro Arg Val
        355                 360                 365
Ala Ala Ser Cys Leu Glu Ala Leu Ala Trp Ile Ala Cys Gly Met Arg
        370                 375                 380
Asp Glu Pro Arg Ala Ala Val Leu Leu Gly Ala Ala Glu Glu Leu Ala
385                 390                 395                 400
Arg Ser Val Gly Ser Ala Val Val Ile Tyr Ser Asp Leu Leu Val Tyr
                    405                 410                 415
His Gln Glu Cys Glu Gln Lys Ser Arg Arg Glu Leu Gly Asp Lys Gly
            420                 425                 430
Phe Ala Ala Tyr Arg Lys Gly Gln Gly Leu Gly Phe Asp Ala Ala
        435                 440                 445
Ile Ala Tyr Ala Leu Arg Glu Gln Pro Ser Thr Ser Gly Pro Thr
        450                 455                 460
Ala Gly Gly Ser Thr Arg Leu Thr Lys Arg Glu Arg Gln Val Ala Gly
465                 470                 475                 480
Leu Ile Ala Glu Gly Leu Thr Asn Gln Ala Ile Ala Asp Arg Leu Val
                    485                 490                 495
Ile Ser Pro Arg Thr Ala Gln Gly His Val Glu His Ile Leu Ala Lys
            500                 505                 510
Leu Gly Phe Thr Ser Arg Ala Gln Val Ala Ala Trp Val Val Glu Arg
        515                 520                 525

Thr Asp Asp Glx
```

-continued

530

<210> SEQ ID NO 4
<211> LENGTH: 1143
<212> TYPE: DNA
<213> ORGANISM: Rhodococcus erythropolis HL PM-1

<400> SEQUENCE: 4

| atggtcgccg gcccttggg tgcgtcgctg ctcgccgatt cggtgccga cgtcatcaag | 60 |
| gtcgagccga tcggcggcga cgagtcgcgg acgttcgggc cgggacgaga cggcatgagt | 120 |
| ggtgtctatt ccggcgtgaa ccgaaacaag cgcgccctcg cgctcgacct tcggacggag | 180 |
| gcgggccgtg acctgttcca cgagctgtgc tcgacagcgg acgtgctcat cgagaacatg | 240 |
| ctgccggcgg tacgggaacg attcgggctg actgccgccg agcttcgcga acggcaccct | 300 |
| cacctgatct gcctcaatgt cagcgggtac ggcgagaccg gccccctcgc gggtcgcccc | 360 |
| gcaatggacc cggtggctca ggcgctcacc ggactcatgc aggcgaccgg tgagcgctcg | 420 |
| gggaggtcgc tcaaggccgg tccgcccgtc gccgacagtg cggcgggcta cctggtcgcg | 480 |
| atcgccgccc tcgtcgcgct cttcgcgaaa cagcgcacgg gggaggggca agtggctcg | 540 |
| gtgtccctgg tgggggcgct gttccatttg cagacgccgt ggctggggca gtacctcctg | 600 |
| gccgactaca tccagggcaa ggtgggcaac ggcagcaatt tctacgcgcc gtacaacgcc | 660 |
| tatacgaccc gtgacggcgg cgcggtgcat gtcgttgcct tcaacgaccg ccacttcgtc | 720 |
| aagctcgccc gggcgatggg tgccgaggct ctgatcgaca tccgcgcttc gcgcaggcc | 780 |
| gcatcccgac tggagaaccg tgaggccctc gacgacgccg tcgcaccctg gttcgccgac | 840 |
| cgcgaccggg acgacgtggt tgcactgctc tcggcccacg acatcatctg tgccccgatt | 900 |
| ctcgcgtacg acgaggccgt caggcatccc cagatccagg cactggacct cgtcgtcgac | 960 |
| atcacccacg acgaactcgg accgctgcag gttccgggtc tcccggtcaa gctctcgggc | 1020 |
| acccgggac acgtacaccg cccaccgacg tcgttgggcg agcacaccac cgagattctc | 1080 |
| agcgatctcg gctacaagga cgaccggatt gcggccctcc gggccgaacg ggtcgtccga | 1140 |
| tga | 1143 |

<210> SEQ ID NO 5
<211> LENGTH: 381
<212> TYPE: PRT
<213> ORGANISM: Rhodococcus erythropolis HL PM-1

<400> SEQUENCE: 5

Met Val Ala Gly Pro Leu Gly Ala Ser Leu Leu Ala Asp Phe Gly Ala
 1               5                  10                  15

Asp Val Ile Lys Val Glu Pro Ile Gly Gly Asp Glu Ser Arg Thr Phe
             20                  25                  30

Gly Pro Gly Arg Asp Gly Met Ser Gly Val Tyr Ser Gly Val Asn Arg
         35                  40                  45

Asn Lys Arg Ala Leu Ala Leu Asp Leu Arg Thr Glu Ala Gly Arg Asp
     50                  55                  60

Leu Phe His Glu Leu Cys Ser Thr Ala Asp Val Leu Ile Glu Asn Met
 65                  70                  75                  80

Leu Pro Ala Val Arg Glu Arg Phe Gly Leu Thr Ala Ala Glu Leu Arg
                 85                  90                  95

Glu Arg His Pro His Leu Ile Cys Leu Asn Val Ser Gly Tyr Gly Glu
            100                 105                 110

```
Thr Gly Pro Leu Ala Gly Arg Pro Ala Met Asp Pro Val Ala Gln Ala
        115                 120                 125
Leu Thr Gly Leu Met Gln Ala Thr Gly Glu Arg Ser Gly Arg Ser Leu
    130                 135                 140
Lys Ala Gly Pro Pro Val Ala Asp Ser Ala Ala Gly Tyr Leu Val Ala
145                 150                 155                 160
Ile Ala Ala Leu Val Ala Leu Phe Ala Lys Gln Arg Thr Gly Glu Gly
                165                 170                 175
Gln Ser Gly Ser Val Ser Leu Val Gly Ala Leu Phe His Leu Gln Thr
            180                 185                 190
Pro Trp Leu Gly Gln Tyr Leu Leu Ala Asp Tyr Ile Gln Gly Lys Val
        195                 200                 205
Gly Asn Gly Ser Asn Phe Tyr Ala Pro Tyr Asn Ala Tyr Thr Thr Arg
    210                 215                 220
Asp Gly Gly Ala Val His Val Ala Phe Asn Asp Arg His Phe Val
225                 230                 235                 240
Lys Leu Ala Arg Ala Met Gly Ala Glu Ala Leu Ile Asp Asp Pro Arg
                245                 250                 255
Phe Ala Gln Ala Ala Ser Arg Leu Glu Asn Arg Glu Ala Leu Asp Asp
            260                 265                 270
Ala Val Ala Pro Trp Phe Ala Asp Arg Asp Arg Asp Val Val Ala
        275                 280                 285
Leu Leu Ser Ala His Asp Ile Ile Cys Ala Pro Ile Leu Ala Tyr Asp
    290                 295                 300
Glu Ala Val Arg His Pro Gln Ile Gln Ala Leu Asp Leu Val Val Asp
305                 310                 315                 320
Ile Thr His Asp Glu Leu Gly Pro Leu Gln Val Pro Gly Leu Pro Val
                325                 330                 335
Lys Leu Ser Gly Thr Pro Gly His Val His Arg Pro Pro Thr Ser Leu
            340                 345                 350
Gly Glu His Thr Thr Glu Ile Leu Ser Asp Leu Gly Tyr Lys Asp Asp
        355                 360                 365
Arg Ile Ala Ala Leu Arg Ala Glu Arg Val Val Arg Glx
    370                 375                 380

<210> SEQ ID NO 6
<211> LENGTH: 888
<212> TYPE: DNA
<213> ORGANISM: Rhodococcus erythropolis HL PM-1

<400> SEQUENCE: 6
atgaaggtcg gaatcaggat cccgggagca ggaccgtggg cagggcccga ggcgatcacg      60
gaggtgtcgc ggttcgctga gaagatcggc ttcgactcgc tctggatgac tgatcatgtg     120
gccttgccga cccgagtcga gacggcgtac ccgtacaccg acgacggcaa gttcctgtgg     180
gatccggcca cgccgtacct cgactgcctc acgtcgttga cgtgggcggc ggccgcgacc     240
gagcggatgg agctcggcac gtcgtgcctc atcctgccgt ggcgtccgct cgtccagacc     300
gccaagacac tggtgagcat cgacgtgatg tcgcgcggcc ggctgtcggt cgccatcggc     360
gtgggctgga tgaaggagca gttcgagctg ctgggagcgc ctttcaagga ccggggggaag    420
cggaccacgg agatggtcaa cgcgatgcgg cacatgtgga aggaagacga ggtcgccttc    480
gacggtgagt ctaccaaact ccacgacttc aagatgtatc cgaagccggt gcggggcacg    540
atccccgtct ggttcgcggg atacagcacc gcctccctgc gccgtatcgc cgccatcggc    600
```

```
gacgggtggc acccattggc gatcgggccg gaggagtacg ccggctacct ggccaccctg      660
aagcaatacg ccgaggaagc cggccgcgac atgaacgaaa tcaccctcac cgcgcggcct      720
ctgcggaagg cgccgtacaa cgccgagacg atcgaagcgt acggcgaact cggtgtcacc      780
cacttcatct gcgacacgtc gttcgagcac gacaccctcg aagcaaccat ggacgagctc      840
gccgagcttg ccgacgccgt cctccccacc gcacacaacc tgccctga                   888
```

<210> SEQ ID NO 7
<211> LENGTH: 296
<212> TYPE: PRT
<213> ORGANISM: Rhodococcus erythropolis HL PM-1

<400> SEQUENCE: 7

```
Met Lys Val Gly Ile Arg Ile Pro Gly Ala Gly Pro Trp Ala Gly Pro
  1               5                  10                  15

Glu Ala Ile Thr Glu Val Ser Arg Phe Ala Glu Lys Ile Gly Phe Asp
             20                  25                  30

Ser Leu Trp Met Thr Asp His Val Ala Leu Pro Thr Arg Val Glu Thr
         35                  40                  45

Ala Tyr Pro Tyr Thr Asp Asp Gly Lys Phe Leu Trp Asp Pro Ala Thr
     50                  55                  60

Pro Tyr Leu Asp Cys Leu Thr Ser Leu Thr Trp Ala Ala Ala Ala Thr
 65                  70                  75                  80

Glu Arg Met Glu Leu Gly Thr Ser Cys Leu Ile Leu Pro Trp Arg Pro
                 85                  90                  95

Leu Val Gln Thr Ala Lys Thr Leu Val Ser Ile Asp Val Met Ser Arg
            100                 105                 110

Gly Arg Leu Ser Val Ala Ile Gly Val Gly Trp Met Lys Glu Gln Phe
        115                 120                 125

Glu Leu Leu Gly Ala Pro Phe Lys Asp Arg Gly Lys Arg Thr Thr Glu
    130                 135                 140

Met Val Asn Ala Met Arg His Met Trp Lys Glu Asp Glu Val Ala Phe
145                 150                 155                 160

Asp Gly Glu Phe Tyr Gln Leu His Asp Phe Lys Met Tyr Pro Lys Pro
                165                 170                 175

Val Arg Gly Thr Ile Pro Val Trp Phe Ala Gly Tyr Ser Thr Ala Ser
            180                 185                 190

Leu Arg Arg Ile Ala Ala Ile Gly Asp Gly Trp His Pro Leu Ala Ile
        195                 200                 205

Gly Pro Glu Glu Tyr Ala Gly Tyr Leu Ala Thr Leu Lys Gln Tyr Ala
    210                 215                 220

Glu Glu Ala Gly Arg Asp Met Asn Glu Ile Thr Leu Thr Ala Arg Pro
225                 230                 235                 240

Leu Arg Lys Ala Pro Tyr Asn Ala Glu Thr Ile Glu Ala Tyr Gly Glu
                245                 250                 255

Leu Gly Val Thr His Phe Ile Cys Asp Thr Ser Phe Glu His Asp Thr
            260                 265                 270

Leu Glu Ala Thr Met Asp Glu Leu Ala Glu Leu Ala Asp Ala Val Leu
        275                 280                 285

Pro Thr Ala His Asn Leu Pro Glx
    290                 295
```

<210> SEQ ID NO 8
<211> LENGTH: 1524
<212> TYPE: DNA

-continued

<213> ORGANISM: Rhodococcus erythropolis HL PM-1

<400> SEQUENCE: 8

```
ttgccgacgc cgtcctcccc accgcacaca acctgccctg acggcccggc ggaagaaagg      60
acgagaattg tgcaggcact cacctcatcg gttcccctcg tcatcggcga ccaactgacc     120
ccatcgtcga cggggcgac cttcgactcg atcaacccgg ccgacgggtc gcacctggcc      180
agcgtcgccg aggccacggc cgcggacgtc gcgcgtgcgg tcgaagccgc gaaggcggcg     240
gccaggacgt ggcagcgcat gcgcccggcc cagcgaaccc gcctgatgtt ccgctacgcc     300
gcgctgatcg aggaacacaa gaccgagctc gcccagctgc agagtcggga catgggcaag     360
cccatccgcg agtcgctcgg gatcgacctg ccgatcatga tcgagacgct cgagtacttc     420
gcgggcctcg tgaccaagat cgagggccga acgacgccgg cgcccggccg tttcctcaac     480
tacaccctgc gtgagccgat cggtgtggtg ggcgccatca ctccctggaa ttttcctgca     540
gtgcaggcgg tctggaagat cgccccggct cttgcgatgg caacgccat cgtgctgaag      600
cctgcgcagc tcgcaccact cgtgcccgtg gcactcggcg agctcgccct cgaggcgggt     660
ctgccgcccg ggctggtcaa cgtcctgccc ggccgcgggt cggtagcggg taacgccttg     720
gtgcagcacc catcggtcgg caaggtgacg ttcaccggct cgaccgaggt cggccagcag     780
atcggccgga tggcggccga ccgcctcatc acggcttcgc tggagctggg cggaaagtct     840
gcgctcgtgg cgttcggcga ctcgtccccg aaggcggtcg cagccgtggt cttccaggcg     900
atgtacagca accagggtga gacctgcacg gcgccgagca ggttgctcgt cgagcggccg     960
atctacgacg aggtggtcga gctcgtccag gcacgtgtcg aggccgcccg ggtgggcgac    1020
ccgctcgacc ccgacacgga gatcggcccg ttgatcagtg ccgagcagcg ggagtcggtc    1080
cactcgtacg tcgtctccgg gaccgaggaa ggcgccacgc tgatcagcgg tggcgaccag    1140
tcgccgaccg gagcgccgga gcagggattc tactaccgtc cgacgctctt ctccggagtc    1200
accgcggaca tgcgcatcgc tcgggaggag atcttcggac ccgtgctgtc ggtgctgccg    1260
ttcgagggag aagaggaggc gatcaccctg ccaacgaca ccgtcttcgg gctggccgcg     1320
ggcgtcttca cccgcgatgt gggccgcgca ctgcggttcg cgcagacgct cgacgccggc    1380
aacgtgtgga tcaacagctg gggagtgctc aacccggcgt cgccgtatcg aggcttcggg    1440
cagagcggct acggcagcga cctcggccag gcggccatcg aaagcttcac caaggagaag    1500
agcatatggg cacgcctgga ctga                                           1524
```

<210> SEQ ID NO 9
<211> LENGTH: 508
<212> TYPE: PRT
<213> ORGANISM: Rhodococcus erythropolis HL PM-1

<400> SEQUENCE: 9

```
Leu Pro Thr Pro Ser Ser Pro Pro His Thr Thr Cys Pro Asp Gly Pro
 1               5                  10                  15

Ala Glu Glu Arg Thr Arg Ile Val Gln Ala Leu Thr Ser Ser Val Pro
             20                  25                  30

Leu Val Ile Gly Asp Gln Leu Thr Pro Ser Ser Thr Gly Ala Thr Phe
         35                  40                  45

Asp Ser Ile Asn Pro Ala Asp Gly Ser His Leu Ala Ser Val Ala Glu
     50                  55                  60

Ala Thr Ala Ala Asp Val Ala Arg Ala Val Glu Ala Ala Lys Ala Ala
 65                  70                  75                  80
```

```
Ala Arg Thr Trp Gln Arg Met Arg Pro Ala Gln Arg Thr Arg Leu Met
                85                  90                  95

Phe Arg Tyr Ala Ala Leu Ile Glu Glu His Lys Thr Glu Leu Ala Gln
            100                 105                 110

Leu Gln Ser Arg Asp Met Gly Lys Pro Ile Arg Glu Ser Leu Gly Ile
        115                 120                 125

Asp Leu Pro Ile Met Ile Glu Thr Leu Glu Tyr Phe Ala Gly Leu Val
    130                 135                 140

Thr Lys Ile Glu Gly Arg Thr Thr Pro Ala Pro Gly Arg Phe Leu Asn
145                 150                 155                 160

Tyr Thr Leu Arg Glu Pro Ile Gly Val Val Gly Ala Ile Thr Pro Trp
                165                 170                 175

Asn Phe Pro Ala Val Gln Ala Val Trp Lys Ile Ala Pro Ala Leu Ala
            180                 185                 190

Met Gly Asn Ala Ile Val Leu Lys Pro Ala Gln Leu Ala Pro Leu Val
        195                 200                 205

Pro Val Ala Leu Gly Glu Leu Ala Leu Glu Ala Gly Leu Pro Pro Gly
    210                 215                 220

Leu Val Asn Val Leu Pro Gly Arg Gly Ser Val Ala Gly Asn Ala Leu
225                 230                 235                 240

Val Gln His Pro Ser Val Gly Lys Val Thr Phe Thr Gly Ser Thr Glu
                245                 250                 255

Val Gly Gln Gln Ile Gly Arg Met Ala Ala Asp Arg Leu Ile Thr Ala
            260                 265                 270

Ser Leu Glu Leu Gly Gly Lys Ser Ala Leu Val Ala Phe Gly Asp Ser
        275                 280                 285

Ser Pro Lys Ala Val Ala Ala Val Val Phe Gln Ala Met Tyr Ser Asn
    290                 295                 300

Gln Gly Glu Thr Cys Thr Ala Pro Ser Arg Leu Leu Val Glu Arg Pro
305                 310                 315                 320

Ile Tyr Asp Glu Val Val Glu Leu Val Gln Ala Arg Val Glu Ala Ala
                325                 330                 335

Arg Val Gly Asp Pro Leu Asp Pro Asp Thr Glu Ile Gly Pro Leu Ile
            340                 345                 350

Ser Ala Glu Gln Arg Glu Ser Val His Ser Tyr Val Val Ser Gly Thr
        355                 360                 365

Glu Glu Gly Ala Thr Leu Ile Ser Gly Gly Asp Gln Ser Pro Thr Gly
    370                 375                 380

Ala Pro Glu Gln Gly Phe Tyr Tyr Arg Pro Thr Leu Phe Ser Gly Val
385                 390                 395                 400

Thr Ala Asp Met Arg Ile Ala Arg Glu Glu Ile Phe Gly Pro Val Leu
                405                 410                 415

Ser Val Leu Pro Phe Glu Gly Glu Glu Ala Ile Thr Leu Ala Asn
            420                 425                 430

Asp Thr Val Phe Gly Leu Ala Ala Gly Val Phe Thr Arg Asp Val Gly
        435                 440                 445

Arg Ala Leu Arg Phe Ala Gln Thr Leu Asp Ala Gly Asn Val Trp Ile
    450                 455                 460

Asn Ser Trp Gly Val Leu Asn Pro Ala Ser Pro Tyr Arg Gly Phe Gly
465                 470                 475                 480

Gln Ser Gly Tyr Gly Ser Asp Leu Gly Gln Ala Ala Ile Glu Ser Phe
                485                 490                 495

Thr Lys Glu Lys Ser Ile Trp Ala Arg Leu Asp Glx
```

<210> SEQ ID NO 10
<211> LENGTH: 1611
<212> TYPE: DNA
<213> ORGANISM: Rhodococcus erythropolis HL PM-1

<400> SEQUENCE: 10

```
atgggcacgc ctggactgac ctccgggaca tcgaggtcac ggaccatcag gcggttgatc      60
gacgcccgcc acacccagga ttggaagcca gcggcggact acacgatcac cgaggacgcc     120
ctcttctcac gcgaccccga cgccgtggcc gtgctgcgcg gggggctcca cacgcccgag     180
aaggtgacgt tcggtcaggt acagcacgcc gctgtgcgcg tcgccggtgt cctccggtcc     240
cgcggggtcg agcccggtga ccgcgtggtc ctgtacctcg accctcggt ggaggccgcc      300
gaggtcgtct tcggggtgct cgtcgccggc ccgtgctcg tgcccgtccc gcgactgctc      360
accggtacct cggtggcgca ccggctcgcc gactcgggcg cgactgtgct ggtcacggac     420
ggtccgggcg tcgaccggct ggagtcgaca ggatgttccc tgcacgacgt cgacgtgctc     480
acggtggacg gcgcccacgg cgcgccgctc ggggacctga cccgccgggt cgaccccgctc    540
gccccggtgc cgcggcggtc ctcggatctt gctctgctga tgtacacgtc gggcaccagc    600
ggcccgccca aggcatcgt tcacggccat cgggtcctgc tcggacatgc gggggtcgac     660
tacgccttcg aactgttcag gccgggtgac gtctatttcg gcactgcgga ctgggggtgg    720
atcggcggcc tgatgctcgg gttgctggtt ccgtggtctc tcggcgttcc tgtcgtggct    780
caccggccgc agcgtttcga tcccggcgcc accctggaca tgctgagccg gtacagcgtg    840
acgaccgcct tcctgccggc gtcggttctt cggatgtttg ccgaacacgg ggaaccggcc    900
cagcggcgtc tgcgggcggt ggtgaccgga ggcgagcccg ccggcgcggt ggaactcggc    960
tgggcccggc ggcatctcag cgacgccgtc aacaaggcct acgtcagac cgaggccaac   1020
gcgctcatcg gcgactccgc tgttctcgga tccgtcgacg acgcgaccat gggcgctccg   1080
tatcccgggc accgcatcgc gctcctggac gacgcgggca ctcacgtcgc gcccggtgag   1140
gtcggtgaga ttgcgctgga acttccggat tcggttgcgc tgctcggcta ttgggatgcg   1200
tcgtcggcta gtgtggtacc tcccgccggg agttggcacc ggacaggcga cctggcacgg   1260
ctcgcacatg gacgccggct ggagtacctc ggccgcgccg acgacgtgat caagagccgc   1320
ggctaccgca tcgtccggc ggagatcgaa gaggcactga gcgtcaccc ccaggtcctg    1380
gacgcggcgg cggtagggct gcccgacccg gagtcggggc agcaggtcaa ggcattcgtc   1440
cacctcgctg ccggcgaact caccgaggag atttcggcgg aactccgtga actcgtcgcc   1500
gccgcggtcg gcccacacgc acgcccccgc gagatagagg cagtcgcagc gttgccgcgc   1560
acggagaccg gaaaggtccg gcggcgggaa ctggtgccgc cctcggctta g            1611
```

<210> SEQ ID NO 11
<211> LENGTH: 537
<212> TYPE: PRT
<213> ORGANISM: Rhodococcus erythropolis HL PM-1

<400> SEQUENCE: 11

```
Met Gly Thr Pro Gly Leu Thr Ser Gly Thr Ser Arg Ser Arg Thr Ile
 1               5                  10                  15

Arg Arg Leu Ile Asp Ala Arg His Thr Gln Asp Trp Lys Pro Ala Ala
             20                  25                  30

Asp Tyr Thr Ile Thr Glu Asp Ala Leu Phe Ser Arg Asp Pro Asp Ala
```

```
            35                  40                  45
Val Ala Val Leu Arg Gly Gly Leu His Thr Pro Glu Lys Val Thr Phe
 50                  55                  60

Gly Gln Val Gln His Ala Ala Val Arg Val Ala Gly Val Leu Arg Ser
 65                  70                  75                  80

Arg Gly Val Glu Pro Gly Asp Arg Val Val Leu Tyr Leu Asp Pro Ser
                 85                  90                  95

Val Glu Ala Ala Glu Val Val Phe Gly Val Leu Val Ala Gly Ala Val
                100                 105                 110

Leu Val Pro Val Pro Arg Leu Leu Thr Gly Thr Ser Val Ala His Arg
                115                 120                 125

Leu Ala Asp Ser Gly Ala Thr Val Leu Val Thr Asp Gly Pro Gly Val
130                 135                 140

Asp Arg Leu Glu Ser Thr Gly Cys Ser Leu His Asp Val Asp Val Leu
145                 150                 155                 160

Thr Val Asp Gly Ala His Gly Ala Pro Leu Gly Asp Leu Thr Arg Arg
                165                 170                 175

Val Asp Pro Leu Ala Pro Val Pro Arg Arg Ser Ser Asp Leu Ala Leu
                180                 185                 190

Leu Met Tyr Thr Ser Gly Thr Ser Gly Pro Pro Lys Gly Ile Val His
                195                 200                 205

Gly His Arg Val Leu Leu Gly His Ala Gly Val Asp Tyr Ala Phe Glu
                210                 215                 220

Leu Phe Arg Pro Gly Asp Val Tyr Phe Gly Thr Ala Asp Trp Gly Trp
225                 230                 235                 240

Ile Gly Gly Leu Met Leu Gly Leu Leu Val Pro Trp Ser Leu Gly Val
                245                 250                 255

Pro Val Val Ala His Arg Pro Gln Arg Phe Asp Pro Gly Ala Thr Leu
                260                 265                 270

Asp Met Leu Ser Arg Tyr Ser Val Thr Thr Ala Phe Leu Pro Ala Ser
                275                 280                 285

Val Leu Arg Met Phe Ala Glu His Gly Glu Pro Ala Gln Arg Arg Leu
                290                 295                 300

Arg Ala Val Val Thr Gly Gly Glu Pro Ala Gly Ala Val Glu Leu Gly
305                 310                 315                 320

Trp Ala Arg Arg His Leu Ser Asp Ala Val Asn Lys Ala Tyr Gly Gln
                325                 330                 335

Thr Glu Ala Asn Ala Leu Ile Gly Asp Ser Ala Val Leu Gly Ser Val
                340                 345                 350

Asp Asp Ala Thr Met Gly Ala Pro Tyr Pro Gly His Arg Ile Ala Leu
                355                 360                 365

Leu Asp Asp Ala Gly Thr His Val Ala Pro Gly Glu Val Gly Glu Ile
370                 375                 380

Ala Leu Glu Leu Pro Asp Ser Val Ala Leu Leu Gly Tyr Trp Asp Ala
385                 390                 395                 400

Ser Ser Ala Ser Val Val Pro Ala Gly Ser Trp His Arg Thr Gly
                405                 410                 415

Asp Leu Ala Arg Leu Ala His Gly Arg Arg Leu Glu Tyr Leu Gly Arg
                420                 425                 430

Ala Asp Asp Val Ile Lys Ser Arg Gly Tyr Arg Ile Gly Pro Ala Glu
                435                 440                 445

Ile Glu Glu Ala Leu Lys Arg His Pro Gln Val Leu Asp Ala Ala Ala
                455                 460
```

```
Val Gly Leu Pro Asp Pro Glu Ser Gly Gln Gln Val Lys Ala Phe Val
465                 470                 475                 480

His Leu Ala Ala Gly Glu Leu Thr Glu Glu Ile Ser Ala Glu Leu Arg
                485                 490                 495

Glu Leu Val Ala Ala Val Gly Pro His Ala Arg Pro Arg Glu Ile
            500                 505                 510

Glu Ala Val Ala Ala Leu Pro Arg Thr Glu Thr Gly Lys Val Arg Arg
            515                 520                 525

Arg Glu Leu Val Pro Pro Ser Ala Glx
        530                 535
```

<210> SEQ ID NO 12
<211> LENGTH: 756
<212> TYPE: DNA
<213> ORGANISM: Rhodococcus erythropolis HL PM-1

<400> SEQUENCE: 12

```
gtgcccgcca tctcgcgcgc aacccgcgta ctcgagacac tggtccagca gtccaccgga      60
gccacactca ccgagttggc caagcggtgc gctctggcga agagcacggc atcggtcctg     120
ctccggacca tggtggtcga gggcctcgtc gtgtacgacc aggagacgcg ccggtacaac     180
ctcggcccgc tgctcgtgga gttcggcgtg gctgcgatcg cgcgaacatc ggcggtcgcc     240
gcgtcgcgga cgtacatgga gtggttggcc gagcggaccg agctggcatg tctcgccatc     300
cagccgatgc cggacggtca cttcacggcg atcgcgaaga tcgagagccg caaggccgtc     360
aaggtcacca tcgaggtcgg ctctcgcttc ggtcgagaca ctccgttgat cagccgactc     420
gcggcggcat ggccgagcag gggtcgcccg gagcttgtcg agtaccccgc cgatgagctc     480
gacgagctcc gggcgcaggg ctacggcgct gtctatggcg aatatcgacc ggaactcaac     540
gtcgtggggg tcccggtgtt cgaccgagac ggcgagccgt gtctgttcat cgccctgctc     600
ggtatcggcg acgatctcac agccgacggt gtggccggga tcgccgacta cctcgtcacg     660
gtttcgcggg agatcagctc gcatatcggc ggccgcattc cggcggacta cccgactcct     720
gtcggggccc ccgacctcgg cgccgggcgc ggctga                               756
```

<210> SEQ ID NO 13
<211> LENGTH: 252
<212> TYPE: PRT
<213> ORGANISM: Rhodococcus erythropolis HL PM-1

<400> SEQUENCE: 13

```
Val Pro Ala Ile Ser Arg Ala Thr Arg Val Leu Glu Thr Leu Val Gln
  1                 5                  10                  15

Gln Ser Thr Gly Ala Thr Leu Thr Glu Leu Ala Lys Arg Cys Ala Leu
                20                  25                  30

Ala Lys Ser Thr Ala Ser Val Leu Leu Arg Thr Met Val Val Glu Gly
            35                  40                  45

Leu Val Val Tyr Asp Gln Glu Thr Arg Arg Tyr Asn Leu Gly Pro Leu
  50                  55                  60

Leu Val Glu Phe Gly Val Ala Ala Ile Ala Arg Thr Ser Ala Val Ala
 65                  70                  75                  80

Ala Ser Arg Thr Tyr Met Glu Trp Leu Ala Glu Arg Thr Glu Leu Ala
                85                  90                  95

Cys Leu Ala Ile Gln Pro Met Pro Asp Gly His Phe Thr Ala Ile Ala
            100                 105                 110
```

```
Lys Ile Glu Ser Arg Lys Ala Val Lys Val Thr Ile Glu Val Gly Ser
            115                 120                 125

Arg Phe Gly Arg Asp Thr Pro Leu Ile Ser Arg Leu Ala Ala Ala Trp
130                 135                 140

Pro Ser Arg Gly Arg Pro Glu Leu Val Glu Tyr Pro Ala Asp Glu Leu
145                 150                 155                 160

Asp Glu Leu Arg Ala Gln Gly Tyr Gly Ala Val Tyr Gly Glu Tyr Arg
                165                 170                 175

Pro Glu Leu Asn Val Val Gly Val Pro Val Phe Asp Arg Asp Gly Glu
                180                 185                 190

Pro Cys Leu Phe Ile Ala Leu Leu Gly Ile Gly Asp Asp Leu Thr Ala
                195                 200                 205

Asp Gly Val Ala Gly Ile Ala Asp Tyr Leu Val Thr Val Ser Arg Glu
            210                 215                 220

Ile Ser Ser His Ile Gly Gly Arg Ile Pro Ala Asp Tyr Pro Thr Pro
225                 230                 235                 240

Val Gly Ala Pro Asp Leu Gly Ala Gly Arg Gly Glx
                245                 250
```

<210> SEQ ID NO 14
<211> LENGTH: 681
<212> TYPE: DNA
<213> ORGANISM: Rhodococcus erythropolis HL PM-1

<400> SEQUENCE: 14

| | |
|---|---|
| atgaagagca gcaagatcgc cgtcgtcggc ggcaccggac cccagggaaa ggggctggcc | 60 |
| taccggttcg cggcggccgg ctggcctgtc gtcatcggat cgcgttctgc cgaacgcgcg | 120 |
| gaggaggcgg ccctcgaggt gcgcagacgc gccggtgacg gcgccgtggt cagcgccgcc | 180 |
| gacaatgcgt cggcagctgc cgactgtccc atcatcctgc tggtcgtccc atacgacggc | 240 |
| catcgtgagc tggtttcgga actggcaccc atcttcgcgg gcaagctcgt cgtcagctgc | 300 |
| gtgaatccgc tcggcttcga caagtccggg gcctacggtt tggacgtcga ggaagggagc | 360 |
| gccgccgagc aactgcgcga cctcgtgccc ggtgccacgg tggtcgctgc ctttcaccat | 420 |
| ctgtcggcgg tcaacctctg gaacatgag ggccccttc ccgaggatgt gctcgtgtgc | 480 |
| ggcgacgatc ggtccgcgaa ggacgaggtg gctcggctcg cagtcgcgat caccggccgg | 540 |
| ccgggcatcg acgaggggc gctgcgggtg gcgcggcagc tcgaaccgtt gaccgccgtt | 600 |
| ctcatcaatg tcaaccggcg ctacaagacg ctctccggtc tcgccgtgaa cggggttgtt | 660 |
| catgatccac gagctgcgtg a | 681 |

<210> SEQ ID NO 15
<211> LENGTH: 227
<212> TYPE: PRT
<213> ORGANISM: Rhodococcus erythropolis HL PM-1

<400> SEQUENCE: 15

```
Met Lys Ser Ser Lys Ile Ala Val Val Gly Gly Thr Gly Pro Gln Gly
1               5                   10                  15

Lys Gly Leu Ala Tyr Arg Phe Ala Ala Ala Gly Trp Pro Val Val Ile
                20                  25                  30

Gly Ser Arg Ser Ala Glu Arg Ala Glu Glu Ala Ala Leu Glu Val Arg
            35                  40                  45

Arg Arg Ala Gly Asp Gly Ala Val Val Ser Ala Ala Asp Asn Ala Ser
        50                  55                  60
```

```
Ala Ala Ala Asp Cys Pro Ile Ile Leu Leu Val Val Pro Tyr Asp Gly
 65                  70                  75                  80

His Arg Glu Leu Val Ser Glu Leu Ala Pro Ile Phe Ala Gly Lys Leu
                 85                  90                  95

Val Val Ser Cys Val Asn Pro Leu Gly Phe Asp Lys Ser Gly Ala Tyr
            100                 105                 110

Gly Leu Asp Val Glu Glu Gly Ser Ala Ala Glu Gln Leu Arg Asp Leu
        115                 120                 125

Val Pro Gly Ala Thr Val Ala Ala Phe His His Leu Ser Ala Val
    130                 135                 140

Asn Leu Trp Glu His Glu Gly Pro Leu Pro Glu Asp Val Leu Val Cys
145                 150                 155                 160

Gly Asp Asp Arg Ser Ala Lys Asp Glu Val Ala Arg Leu Ala Val Ala
                165                 170                 175

Ile Thr Gly Arg Pro Gly Ile Asp Gly Gly Ala Leu Arg Val Ala Arg
            180                 185                 190

Gln Leu Glu Pro Leu Thr Ala Val Leu Ile Asn Val Asn Arg Arg Tyr
        195                 200                 205

Lys Thr Leu Ser Gly Leu Ala Val Asn Gly Val Val His Asp Pro Arg
210                 215                 220

Ala Ala Glx
225

<210> SEQ ID NO 16
<211> LENGTH: 1050
<212> TYPE: DNA
<213> ORGANISM: Rhodococcus erythropolis HL PM-1

<400> SEQUENCE: 16
atgatcaaag gcatccagct ccatggttgg gctgacgggc cgcagatggt cgaagtggcc      60
gagatcgccg ctgggagttt cgaaaccgtc tggctcagtg accaactcca gtcccgaggc     120
gtcgccgttc tcctcggcgc aatcgctgcg cgcaccggtg tcggagtcgg cactgcagtg     180
accttccct tcgggcggaa ccccctcgag atggcatcca gcatggccac cctggcggag     240
ttcatgcccg aaggacgtcg ggtcaccatg ggaatcggca ccggaggtgg gctggtgagt     300
gcgctcatgc cgctgcagaa cccgatcgac cgcgtggccg agttcatcgc gatgtgccgg     360
cttctctggc agggcgaagc gatccgaatg ggtgactacc acagatctg taccgccctc      420
ggcttgcgtg aggatgctcg ggcgtcgttc tcctggacga gcaagcccga cgtgcgcgtc     480
gtcgtcgccg gcgccggacc gaaagtgctg gagatggccg cgaactcgc agacggcgtc      540
atctgcgcca gcaatttccc ggcccacagc ctcgcgcct tccgtagcgg ccagttcgac      600
gcggtgagca acctcgatgc gctcgaccgg ggccgaaagc gcagtcggcg ggggagttc       660
acccggatct acgcgtgaa cctgtccgtg tctgccgacc gggagagtgc ctgcgcggcc      720
gcgcggcgac aggcgacact cattgtgagc aacagcctc cagagaatct gcaccgggtc      780
ggctttgagc cctccgacta cgccgccacc cgagcggcgc tcaaagccgg agacggcgta    840
gacgcagccg ccgacctcct cccacaggaa gtcgcggacc aactcgtggt ctcgggcacg     900
cccggcgact gcatcgaggc gctggccgag ctgctcgggt acgcggagga tgccggattc    960
accgaggcct acatcggtgc cccggtcggc ccggacccac gcgaggcggt cgagctcctc    1020
acgtcccagg tcctgccgga gctcgcatga                                    1050

<210> SEQ ID NO 17
```

```
<211> LENGTH: 350
<212> TYPE: PRT
<213> ORGANISM: Rhodococcus erythropolis HL PM-1

<400> SEQUENCE: 17

Met Ile Lys Gly Ile Gln Leu His Gly Trp Ala Asp Gly Pro Gln Met
  1               5                  10                  15

Val Glu Val Ala Glu Ile Ala Ala Gly Ser Phe Glu Thr Val Trp Leu
                 20                  25                  30

Ser Asp Gln Leu Gln Ser Arg Gly Val Ala Val Leu Leu Gly Ala Ile
             35                  40                  45

Ala Ala Arg Thr Gly Val Gly Val Gly Thr Ala Val Thr Phe Pro Phe
         50                  55                  60

Gly Arg Asn Pro Leu Glu Met Ala Ser Ser Met Ala Thr Leu Ala Glu
 65                  70                  75                  80

Phe Met Pro Glu Gly Arg Arg Val Thr Met Gly Ile Gly Thr Gly Gly
                 85                  90                  95

Gly Leu Val Ser Ala Leu Met Pro Leu Gln Asn Pro Ile Asp Arg Val
                100                 105                 110

Ala Glu Phe Ile Ala Met Cys Arg Leu Leu Trp Gln Gly Glu Ala Ile
            115                 120                 125

Arg Met Gly Asp Tyr Pro Gln Ile Cys Thr Ala Leu Gly Leu Arg Glu
        130                 135                 140

Asp Ala Arg Ala Ser Phe Ser Trp Thr Ser Lys Pro Asp Val Arg Val
145                 150                 155                 160

Val Val Ala Gly Ala Gly Pro Lys Val Leu Glu Met Ala Gly Glu Leu
                165                 170                 175

Ala Asp Gly Val Ile Cys Ala Ser Asn Phe Pro Ala His Ser Leu Ala
            180                 185                 190

Ala Phe Arg Ser Gly Gln Phe Asp Ala Val Ser Asn Leu Asp Ala Leu
        195                 200                 205

Asp Arg Gly Arg Lys Arg Ser Arg Arg Gly Glu Phe Thr Arg Ile Tyr
    210                 215                 220

Gly Val Asn Leu Ser Val Ser Ala Asp Arg Glu Ser Ala Cys Ala Ala
225                 230                 235                 240

Ala Arg Arg Gln Ala Thr Leu Ile Val Ser Gln Pro Pro Glu Asn
                245                 250                 255

Leu His Arg Val Gly Phe Glu Pro Ser Asp Tyr Ala Ala Thr Arg Ala
                260                 265                 270

Ala Leu Lys Ala Gly Asp Gly Val Asp Ala Ala Asp Leu Leu Pro
        275                 280                 285

Gln Glu Val Ala Asp Gln Leu Val Val Ser Gly Thr Pro Gly Asp Cys
    290                 295                 300

Ile Glu Ala Leu Ala Glu Leu Leu Gly Tyr Ala Glu Asp Ala Gly Phe
305                 310                 315                 320

Thr Glu Ala Tyr Ile Gly Ala Pro Val Gly Pro Asp Pro Arg Glu Ala
                325                 330                 335

Val Glu Leu Leu Thr Ser Gln Val Leu Pro Glu Leu Ala Glx
                340                 345                 350

<210> SEQ ID NO 18
<211> LENGTH: 711
<212> TYPE: DNA
<213> ORGANISM: Rhodococcus erythropolis HL PM-1

<400> SEQUENCE: 18
```

```
atgagcgccg gcacgcaggc aacccgggac ctgtgcccgg ccgaacacca cgacggtctg    60
gtcgtcctga cgctcaatcg tcccgaggcg cgcaacgccc tcgacgtacc cctgctcgag   120
gcgttcgccg ctcggcttgc cgagggaaaa cgcgcgggcg ccggcgtcgt cctcgtgcgc   180
gcggaagggc cggcgttctg cgcaggagcg gatgtgcgtt ccgacgacgg cacggcgacc   240
ggccgaccgg gcctccggcg ccgtctcatc gaggagagcc tcgacctgct gggcgactac   300
ccggcggcgg tggtcgcggt gcagggcgcc gcgatcggcg ccgggtgggc aatagccgcg   360
gcagcggaca tcacgctggc ctcgcctacc gcttcgttcc gatttcccga gctcccactc   420
ggattcccgc ccctgacag cacggtgcgc atactcgaag ccgccgtcgg cccggcgcgg   480
gcgctgcggc tcctggccct gaacgagcgc ttcgtcgccg acgacctggc caggctcggt   540
ctggtggacg tcgttcccga ggattcgctc gacgtgacgg cgcgcgagac ggccgcccga   600
ctcgcggttc ttccctcga gttgctgcgc gatctcaaaa caggcctctc cgccgggaag   660
cggcccccct ccatcgaccg accagcctcg aaaggcagtc atgagcacta g            711
```

<210> SEQ ID NO 19
<211> LENGTH: 237
<212> TYPE: PRT
<213> ORGANISM: Rhodococcus erythropolis HL PM-1

<400> SEQUENCE: 19

```
Met Ser Ala Gly Thr Gln Ala Thr Arg Asp Leu Cys Pro Ala Glu His
  1               5                  10                  15

His Asp Gly Leu Val Val Leu Thr Leu Asn Arg Pro Glu Ala Arg Asn
                 20                  25                  30

Ala Leu Asp Val Pro Leu Leu Glu Ala Phe Ala Ala Arg Leu Ala Glu
             35                  40                  45

Gly Lys Arg Ala Gly Ala Gly Val Val Leu Val Arg Ala Glu Gly Pro
         50                  55                  60

Ala Phe Cys Ala Gly Ala Asp Val Arg Ser Asp Asp Gly Thr Ala Thr
 65                  70                  75                  80

Gly Arg Pro Gly Leu Arg Arg Leu Ile Glu Glu Ser Leu Asp Leu
                 85                  90                  95

Leu Gly Asp Tyr Pro Ala Ala Val Val Ala Val Gln Gly Ala Ala Ile
                100                 105                 110

Gly Ala Gly Trp Ala Ile Ala Ala Ala Asp Ile Thr Leu Ala Ser
            115                 120                 125

Pro Thr Ala Ser Phe Arg Phe Pro Glu Leu Pro Leu Gly Phe Pro Pro
        130                 135                 140

Pro Asp Ser Thr Val Arg Ile Leu Glu Ala Ala Val Gly Pro Ala Arg
145                 150                 155                 160

Ala Leu Arg Leu Leu Ala Leu Asn Glu Arg Phe Val Ala Asp Asp Leu
                165                 170                 175

Ala Arg Leu Gly Leu Val Asp Val Val Pro Glu Asp Ser Leu Asp Val
            180                 185                 190

Thr Ala Arg Glu Thr Ala Ala Arg Leu Ala Val Leu Pro Leu Glu Leu
        195                 200                 205

Leu Arg Asp Leu Lys Thr Gly Leu Ser Ala Gly Lys Arg Pro Pro Ser
    210                 215                 220

Ile Asp Arg Pro Ala Ser Lys Gly Ser His Glu His Glx
225                 230                 235
```

```
<210> SEQ ID NO 20
<211> LENGTH: 1083
<212> TYPE: DNA
<213> ORGANISM: Rhodococcus erythropolis HL PM-1

<400> SEQUENCE: 20
atgagcacta gcattcacat tcagaccgac gagcaggcgc acctccgcac cactgcccgg      60
gcattcctgg ccagacacgc tcccgcgctc gacgtgcgca tctgggacga ggcggggaaa    120
taccccgagc acctgttccg cgagatcgcc cgcctcgggt ggtacgacgt ggtggccgga    180
gacgaggtcg tcgacggtac ggccggcctg ctgatcacgc tctgcgaaga gatcggccgg    240
gcgagttcgg acctcgtggc cttgttcaac ctgaacctca gtgggctgcg cgacatccac    300
cgctggggca cgcccgaaca gcaggagacg tacggtgcac cggtgctggc cggcgaggcg    360
cgcctgtcga tcgcggtgag cgaacccgac gtgggctcgg acgccgcgag cgtggccacg    420
cgcgccgaga aggtcgggga ctcgtggatc ctcaacggcc agaagaccta ctgcgagggc    480
gcgggactaa ccggcgcagt aatggaactc gtcgcccgag tgggaggggg tggtcgcaag    540
cgcgaccaac tcgccatatt tctggtgccg gtcgatcatc cggggtcga ggtccgccgc    600 atgcccgcgc tcggccggaa catcagcggc atctacgagg tcttcctgcg ggacgttgcg    660
cttccggcga cggcggtgct gggtgagccc ggtgaaggat ggcagatcct caaggaacgt    720
ctggtgctcg agcggatcat gatcagttcc ggcttcctcg gcagcgtcgc cgcggtactc    780
gacctgacgg tccactacgc caacgagcgc gagcagttcg gcaaggcact ctcgagctat    840
cagggcgtga ccttgcccct cgccgagatg ttcgtcaggc tcgacgcggc ccagtgcgcg    900
gtacgccgtt cggccgacct cttcgacgcg gtctgccgt gcgaggtgga gagcacgatg    960
gcgaagttcc tctccggcca gctctacgcg gaggcctctg ctctggcgat gcagattcag   1020
ggcgcctacg gctatgtgcg cgaccatgcc ttgccgatgc accactccga cgggatcccc   1080
ggg                                                                 1083

<210> SEQ ID NO 21
<211> LENGTH: 361
<212> TYPE: PRT
<213> ORGANISM: Rhodococcus erythropolis HL PM-1

<400> SEQUENCE: 21

Met Ser Thr Ser Ile His Ile Gln Thr Asp Glu Gln Ala His Leu Arg
  1               5                  10                  15

Thr Thr Ala Arg Ala Phe Leu Ala Arg His Ala Pro Ala Leu Asp Val
             20                  25                  30

Arg Ile Trp Asp Glu Ala Gly Lys Tyr Pro Glu His Leu Phe Arg Glu
         35                  40                  45

Ile Ala Arg Leu Gly Trp Tyr Asp Val Val Ala Gly Asp Glu Val Val
     50                  55                  60

Asp Gly Thr Ala Gly Leu Leu Ile Thr Leu Cys Glu Glu Ile Gly Arg
 65                  70                  75                  80

Ala Ser Ser Asp Leu Val Ala Leu Phe Asn Leu Asn Leu Ser Gly Leu
                 85                  90                  95

Arg Asp Ile His Arg Trp Gly Thr Pro Glu Gln Gln Glu Thr Tyr Gly
            100                 105                 110

Ala Pro Val Leu Ala Gly Glu Ala Arg Leu Ser Ile Ala Val Ser Glu
        115                 120                 125

Pro Asp Val Gly Ser Asp Ala Ala Ser Val Ala Thr Arg Ala Glu Lys
    130                 135                 140
```

-continued

```
Val Gly Asp Ser Trp Ile Leu Asn Gly Gln Lys Thr Tyr Cys Glu Gly
145                 150                 155                 160

Ala Gly Leu Thr Gly Ala Val Met Glu Leu Val Ala Arg Val Gly Gly
            165                 170                 175

Gly Gly Arg Lys Arg Asp Gln Leu Ala Ile Phe Leu Val Pro Val Asp
        180                 185                 190

His Pro Gly Val Glu Val Arg Met Pro Ala Leu Gly Arg Asn Ile
    195                 200                 205

Ser Gly Ile Tyr Glu Val Phe Leu Arg Asp Val Ala Leu Pro Ala Thr
    210                 215                 220

Ala Val Leu Gly Glu Pro Gly Glu Gly Trp Gln Ile Leu Lys Glu Arg
225                 230                 235                 240

Leu Val Leu Glu Arg Ile Met Ile Ser Ser Gly Phe Leu Gly Ser Val
                245                 250                 255

Ala Ala Val Leu Asp Leu Thr Val His Tyr Ala Asn Glu Arg Glu Gln
                260                 265                 270

Phe Gly Lys Ala Leu Ser Ser Tyr Gln Gly Val Thr Leu Pro Leu Ala
            275                 280                 285

Glu Met Phe Val Arg Leu Asp Ala Ala Gln Cys Ala Val Arg Arg Ser
290                 295                 300

Ala Asp Leu Phe Asp Ala Gly Leu Pro Cys Glu Val Glu Ser Thr Met
305                 310                 315                 320

Ala Lys Phe Leu Ser Gly Gln Leu Tyr Ala Glu Ala Ser Ala Leu Ala
                325                 330                 335

Met Gln Ile Gln Gly Ala Tyr Gly Tyr Val Arg Asp His Ala Leu Pro
                340                 345                 350

Met His His Ser Asp Gly Ile Pro Gly
                355                 360

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:primer
<221> NAME/KEY: unsure
<222> LOCATION: (13)..(17)
<223> OTHER INFORMATION: V represent all the combinations of the three
      bases A, G and C at the last 5 positions of the 3' end

<400> SEQUENCE: 22
cggagcagat cgvvvvv                                                  17

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 23
agtccacgga gcatatcg                                                 18

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence:primer
<223> OTHER INFORMATION: Common region of the 240 primers used in the
```

-continued instant invention

<400> SEQUENCE: 24
cggagcagat cg                                                         12

<210> SEQ ID NO 25
<211> LENGTH: 82
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 25

Gly Ala Asp Arg Thr Lys Ala Ile Thr Met Thr Ala Gln Ile Ser Pro
 1               5                  10                  15

Thr Val Val Asp Ala Val Val Ile Gly Ala Gly Phe Ala Asp Leu Arg
            20                  25                  30

Arg Ala Gln Ala Ala Gln Arg Thr Gly Pro Asp Arg Gly Arg Phe Arg
        35                  40                  45

Gln Gly Gly Arg Pro Arg Arg Tyr Leu Val Leu Glu Pro Leu Pro Gly
    50                  55                  60

Gly Ala Leu Arg His Arg Glu Ser Ser Leu Pro Leu Leu Val Arg Ser
65                  70                  75                  80

Ala Pro

<210> SEQ ID NO 26
<211> LENGTH: 95
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 26

Glu Gln Ile Glu Thr Gln Val Glu Trp Ile Ser Asp Thr Val Ala Tyr
 1               5                  10                  15

Ala Glu Arg Asn Glu Ile Arg Ala Ile Glu Pro Thr Pro Glu Ala Glu
            20                  25                  30

Glu Glu Trp Thr Gln Thr Cys Thr Asp Ile Ala Asn Ala Thr Leu Phe
        35                  40                  45

Thr Arg Gly Asp Ser Trp Ile Phe Gly Ala Asn Val Pro Gly Lys Lys
    50                  55                  60

Pro Ser Val Leu Phe Tyr Leu Gly Gly Leu Gly Asn Tyr Arg Asn Val
65                  70                  75                  80

Leu Ala Gly Val Val Ala Asp Ser Tyr Arg Gly Phe Glu Leu Lys
                85                  90                  95

<210> SEQ ID NO 27
<211> LENGTH: 51
<212> TYPE: PRT
<213> ORGANISM: Unknown Organism
<220> FEATURE:
<223> OTHER INFORMATION: Description of Unknown Organism:  microbial
      enrichment culture-not one single organism

<400> SEQUENCE: 27

Ala Thr Leu Phe Thr Lys Gly Asp Ser Trp Ile Phe Gly Ala Asn Ile
 1               5                  10                  15

Pro Gly Lys Thr Pro Ser Val Leu Phe Tyr Leu Gly Gly Leu Arg Asn
            20                  25                  30

-continued

Tyr Arg Ala Val Leu Ala Glu Val Ala Thr Asp Gly Tyr Arg Gly Phe
          35                  40                  45

Asp Val Lys
     50

<210> SEQ ID NO 28
<211> LENGTH: 92
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 28

Ile Glu Thr Gln Val Glu Trp Ile Ser Asp Thr Val Pro Thr Pro Ser
 1               5                  10                  15

Ala Thr Arg Ser Val Arg Ser Asn Pro Pro Arg Ser Arg Gly Gly Val
            20                  25                  30

Asp Ala Asp Leu His Arg His Arg Glu Pro Thr Leu Phe Thr Arg Gly
        35                  40                  45

Asp Ser Trp Ile Phe Gly Ala Asn Val Pro Gly Lys Lys Pro Ser Val
    50                  55                  60

Leu Phe Tyr Leu Gly Gly Leu Gly Asn Tyr Arg Asn Val Leu Ala Gly
65                  70                  75                  80

Val Val Ala Asp Ser Tyr Arg Gly Phe Glu Leu Lys
                85                  90

<210> SEQ ID NO 29
<211> LENGTH: 88
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 29

Glu Trp Ile Ser Asp Thr Ile Gly Tyr Ala Glu Arg Asn Gly Val Arg
 1               5                  10                  15

Ala Ile Glu Pro Thr Pro Glu Ala Glu Ala Arg Met Asp Arg Asp Leu
            20                  25                  30

His Arg Asp Arg Asp Ala Thr Leu Phe Thr Lys Gly Asp Ser Trp Ile
        35                  40                  45

Phe Gly Ala Asn Ile Pro Gly Lys Thr Pro Ser Val Leu Phe Tyr Leu
    50                  55                  60

Gly Gly Leu Arg Asn Tyr Arg Ala Val Leu Ala Glu Val Ala Thr Asp
65                  70                  75                  80

Gly Tyr Arg Gly Phe Asp Val Lys
                85

<210> SEQ ID NO 30
<211> LENGTH: 59
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 30

Pro Met Gly Val Tyr Thr Thr Ile Asp Pro Ala Thr Gly Asp Ala Thr
 1               5                  10                  15

```
Ala Gln Tyr Pro Lys Ile Ser Asp Ala Glu Leu Asp Thr Leu Ile Lys
                20                  25                  30

Asn Ser Ala Ala Ala Tyr Arg Ser Trp Arg Thr Thr Thr Leu Glu Gln
         35                  40                  45

Arg Arg Ala Val Leu Thr Arg Thr Ala Ser Ile
     50                  55
```

<210> SEQ ID NO 31
<211> LENGTH: 91
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 31

```
Asp Gln Ser Lys Val Leu Leu Tyr Thr His Gly Gly Phe Ala Val
 1               5                  10                  15

Gly Ser Pro Pro Ser His Arg Lys Leu Ala Ala His Val Ala Lys Ala
                20                  25                  30

Leu Gly Ser Val Ser Phe Val Leu Asp Tyr Arg Ala Pro Pro Asn Ser
         35                  40                  45

Ser Thr Arg His Arg Ser Lys Thr Trp Pro Pro Ser Met Pro Ser Ser
     50                  55                  60

Pro Ala Ser Pro Leu Arg Thr Ser Pro Pro Ser Val Ile Pro Gly Gly
65                  70                  75                  80

Asn Leu Ala Ile Ala Ile Ala Leu Asp Leu Leu
                85                  90
```

<210> SEQ ID NO 32
<211> LENGTH: 73
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 32

```
Lys His Thr Tyr Ile Thr Gln Pro Glu Ile Leu Glu Tyr Leu Glu Asp
 1               5                  10                  15

Val Val Asp Arg Phe Asp Leu Arg Arg Thr Phe Arg Phe Gly Thr Glu
                20                  25                  30

Val Lys Ser Ala Thr Tyr Leu Glu Asp Glu Gly Leu Trp Glu Val Thr
         35                  40                  45

Thr Gly Gly Gly Ala Val Tyr Arg Ala Lys Tyr Val Ile Asn Ala Val
     50                  55                  60

Gly Leu Leu Ser Ala Ile Asn Phe Pro
65                  70
```

<210> SEQ ID NO 33
<211> LENGTH: 72
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 33

```
Arg Gly Val Glu Glu Leu Asp Glu Leu Val Gln Gly Arg Ser Ser His
 1               5                  10                  15

Gly Ala Lys Leu Leu Leu Gly Gly Glu Arg Pro Asp Gly Pro Gly Ala
```

-continued

```
                    20                  25                  30

Tyr Tyr Pro Ala Thr Val Leu Ala Gly Val Thr Pro Ala Met Arg Ala
            35                  40                  45

Phe Thr Glu Glu Leu Phe Gly Pro Val Ala Val Tyr Arg Val Gly
        50                  55                  60

Ser Leu Gln Glu Ala Ile Asp Leu
65                  70

<210> SEQ ID NO 34
<211> LENGTH: 52
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 34

Ala Glu Glu Glu Trp Thr Gln Thr Cys Thr Asp Ile Ala Glu Pro Thr
1               5                   10                  15

Leu Phe Thr Arg Gly Asp Ser Trp Ile Phe Gly Ala Asn Val Pro Gly
            20                  25                  30

Lys Lys Pro Ser Val Leu Phe Tyr Pro Gly Gly Leu Gly Asn Tyr Arg
        35                  40                  45

Asn Val Leu Ala
    50

<210> SEQ ID NO 35
<211> LENGTH: 51
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 35

Ile Ala Glu Ser Gly Phe Gly Ser Leu Thr Ile Glu Gly Val Ala Glu
1               5                   10                  15

Arg Ser Gly Val Ala Lys Thr Thr Ile Tyr Arg Arg His Arg Ser Arg
            20                  25                  30

Asn Asp Leu Ala Leu Ala Val Leu Leu Asp Met Val Gly Asp Val Ser
        35                  40                  45

Thr Gln Pro
    50

<210> SEQ ID NO 36
<211> LENGTH: 41
<212> TYPE: PRT
<213> ORGANISM: Unknown Organism
<220> FEATURE:
<223> OTHER INFORMATION: Description of Unknown Organism: microbial
      enrichment culture-not one single organism

<400> SEQUENCE: 36

Ala Arg Thr Glu Arg Ala Val Met Asp Ala Ala Arg Glu Leu Leu Ala
1               5                   10                  15

Glu Ser Gly Phe Gly Ser Leu Thr Ile Glu Gly Val Ala Glu Arg Ser
            20                  25                  30

Gly Val Ala Lys Thr Thr Ile Tyr Arg
        35                  40

<210> SEQ ID NO 37
```

-continued

```
<211> LENGTH: 52
<212> TYPE: PRT
<213> ORGANISM: Unknown Organism
<220> FEATURE:
<223> OTHER INFORMATION: Description of Unknown Organism:  microbial
      enrichment culture-not one single organism

<400> SEQUENCE: 37

Gln Ile Ala Glu Ile Ile Glu Asp Pro Glu Thr Ala Arg Lys Leu Met
 1               5                  10                  15

Pro Thr Gly Leu Tyr Ala Lys Arg Pro Leu Cys Asp Asn Gly Tyr Tyr
             20                  25                  30

Glu Val Tyr Asn Arg Pro Asn Val Glu Ala Val Ala Ile Lys Glu Asn
         35                  40                  45

Pro Ile Arg Glu
     50
```

HIGH DENSITY SAMPLING OF DIFFERENTIALLY EXPRESSED PROKARYOTIC MRNA

This application claims the benefit of U.S. Provisional Application No. 60/152,542 filed Sep. 3, 1999.

FIELD OF THE INVENTION

This invention relates to the field of molecular biology and microbiology. More specifically, this invention describes a technique to identify inducible genes in microbes, in particular prokaryotes using a large number of arbitrarily primed PCR reactions.

BACKGROUND OF THE INVENTION

Traditionally, the cloning of useful metabolic genes has been performed either through a direct genetic approach or by the "reverse genetics" approach. These methods involve purification of an enzyme of interest followed by the identification of its gene through the use of antibodies or amino acid sequence information obtained from the pure protein.

Although both strategies are routinely used, they are often limited by technical problems. The genetic approach can only be used for organisms that have a developed genetic system or whose genes can be expressed in heterologous hosts. The reverse genetics approach requires the purification of the protein of interest, amino acid sequencing, further determination of DNA sequence and amplification of a DNA probe from degenerate primers. Both approaches are time consuming and inefficient.

Recently, mRNA techniques that can be employed to access regulated genes directly in the absence of a genetic system and without the purification of their gene products have been disclosed. These approaches are based on the comparison of the mRNA population between two cultures or tissues, and further identification of the genes or a subset of genes whose mRNA is more abundant under conditions of induction. These techniques rely on various methods including: 1) hybridization of labeled mRNAs onto arrays of DNA on membranes (Chuang et al., *J. Bacteriol.* 175:5242–5252 (1993)), 2) DNA microarrays (Duggan et al., *Nat. Genet.* 21:10–14 (1999)), 3) large scale sample sequencing of EST libraries (Rafalski et al., *Acta Biochimica Polonica* 45:929–934 (1998)), and 4) the sampling of mRNA by the production of randomly amplified DNA fragments by reverse transcription followed by polymerase chain reaction (RT-PCR).

Two variations of sampling of mRNA by the production of arbitrarily amplified DNA fragments by reverse transcription followed by RT-PCR have been published. The first one, differential display per se, (DD) (Liang et al., *Science* 257:967–971 (1992), Liang et al., *Nucleic Acids Res.* 21:3269–3275 (1993)) starts with the synthesis of cDNAs by reverse transcription of mRNA using a poly-dT primer that hybridizes to the poly-A tail of eukaryotic messages. Synthesis of the second DNA strand is then initiated at random sites under low stringency using an oligonucleotide of arbitrary sequence. Subsequent exponential amplification by PCR yields a series of DNA fragments in a process essentially identical to that of random amplification of polymorphic DNA (RAPD) (Williams et al., *Nucleic Acids Res.* 18:6531–6535 (1990)). This technique is commonly used for eukaryotic applications.

The second method uses an arbitrary oligonucleotide primer to initiate reverse transcription of the message at random sites. This technique is independent of poly(A) tails, and can be used for both eukaryotic and procaryotic cells (Welsh et al., *Nucleic Acids Res.* 20:4965–4970 (1992)). In spite of this teaching only a handful of prokaryotic applications of DD have been published to date, (Abu Kwaik et al., *Mol. Microbiol.* 21:543–556 (1996); Fleming et al., *Appl. Environ. Microbiol.* 64:3698–3706 (1998); Wong et al., *Proc. Natl. Acad. Sci. USA* 91:639–643 (1994); Yuk et al., *Mol. Microbiol.* 28:945–959 (1998)); Zhang et al., *Science* 273:1234–1236 (1996)), suggesting difficulties with the method.

The above cited methods are useful for the identification of selected inducible genes, however, suffer from several drawbacks when applied to the problem of identifying gene clusters and metabolic pathways, particularly in prokaryotic organisms. These drawbacks include: (i) the short half life of prokaryotic mRNA make any mRNA-based experiment more difficult than in eukaryotic systems, (ii) differential display often results in a high number of false positives and (iii) current literature protocols are very cumbersome and time consuming. No method is available which addresses these drawbacks and definitively distinguishes between false positives and those gene which are are truly differentially expressed.

The problem to be solved, therefore is to develop a reliable system for identifying inducible genes in prokaryotic systems. Applicants have solved the stated problem by providing a method for high density sampling of a mRNA population using a large number of arbitrary primers where a single mRNA molecule is sampled repeatedly in independent RT-PCR reactions. The present invention represents a significant advance in the art, as the literature teaches only applications of differential display which use a small set of primers in a single RT-PCR reaction to generate many differentially amplified bands corresponding to differentially expressed genes which is then analyzed by long high resolution sequencing gels (Liang et al., *Science* 257:967–971 (1992), Wong et al., *Proc. Natl. Acad. Sci. USA* 91:639–643 (1994), Fleming et al., *Appl. Environ. Microbiol.* 64:3698–3706 (1998)). Using this method Applicants were able to identify 21 induced gene fragments, all of which were functionally related. To date, the greatest number of primers used in a similar method is 32 (Rivera-Marrero et al., *Microb Pathog* 25 (6):307 (1998)), resulting in only the identification of 4 induced genes. Abu Kwaik et al., (*Mol. Microbiol.* 21:543–556 (1996), using 30 primers was only able to identify 1 induced gene.

The present method of multiple sampling of RNA is particularly suitable for prokaryotic applications where RNA messages are polycistronic and thus constitute a larger target for arbitrary amplification by RT-PCR and which would permit the identification of more full length genes.

SUMMARY OF THE INVENTION

The present invention provides a method for the high density sampling of differentially displayed genes in prokaryotic organisms, providing for the identification of functionally related genes. The discovery of metabolic genes are particularly amenable to this method because, (i) metabolic gene messages are maintained at base line levels while not induced; and (ii) when required by cell growth and upon induction, metabolic cells are highly expressed, resulting in an increase in steady-state levels of mRNA producing abundant message for sampling.

The strength of the present method lies in the fact that only a physiological characterization of the desired biochemistry is needed. The present method is particularly useful because the method; (i) can be performed in isolates for which genetic systems have not been developed; and (ii) can overcome the deficiencies of homology based methods which are subject to complications caused by significant divergence within a gene family.

Therefore the present invention provides a method for the identification of differentially expressed genes comprising: (i) separating a first and second population of microbial cells, where the first population of cells is contacted with an stimulating agent; (ii) extracting total RNA from the first and second population of microbial cells of step (i); (iii) amplifying the extracted RNA of the first and second populations of microbial cells by a process comprising: a) preparing a collection of at least 32 different arbitrary primers, each primer comprising a common region and a variable region; b) individually contacting each different primer of step (a) with a sample of the extracted RNA from the first and second population of microbial cells under conditions where a set of first and second amplification products are produced; (iv) purifying the first and second amplification products of step (iii); (v) identifying the amplification products generated from the first population of microbial cells that differ from the amplification products generated from the second population of microbial cells as differentially expressed genes; and (vi) optionally sequencing the identified differentially expressed genes of step (v).

Additionally, the invention provides a method for distinguishing genetic differences between two populations of cells comprising: (i) separating a first and second population of microbial cells, where the first population of cells where the first and second populations of cells differ in genotype; (ii) extracting total RNA from the first and second population of microbial cells of step (i); (iii) amplifying the extracted RNA of the first and second populations of microbial cells by a process comprising:

a) preparing a collection of at least 32 different arbitrary primers, each primer comprising a common region and a variable region;

b) individually contacting each different primer of step (a) with a sample of the extracted RNA from the first and second population of microbial cells under conditions where a set of first and second amplification products are produced;

(iv) purifying the first and second amplification products of step (iii); (v) identifying the amplification products generated from the first population of microbial cells that differ from the amplification products generated from the second population of microbial cells; and (vi) optionally sequencing the identified genes of step (v). The invention additionally provides that the first and second amplification products may be produced under low stringency conditions and that the first and second population of cells may either be pure cultures or a consortium of microbes.

The invention further provides a random primer having the sequence 5'-CGGAGCAGATCGVVVVV-3' wherein each V may be independently selected from the group of bases consisting of A, G, and C.

BRIEF DESCRIPTION OF THE DRAWINGS AND SEQUENCE DESCRIPTIONS

FIG. 1 presents a diagram showing the induction of the degradation of picric acid and DNP by DNP in respirometry experiments.

Figure 2:
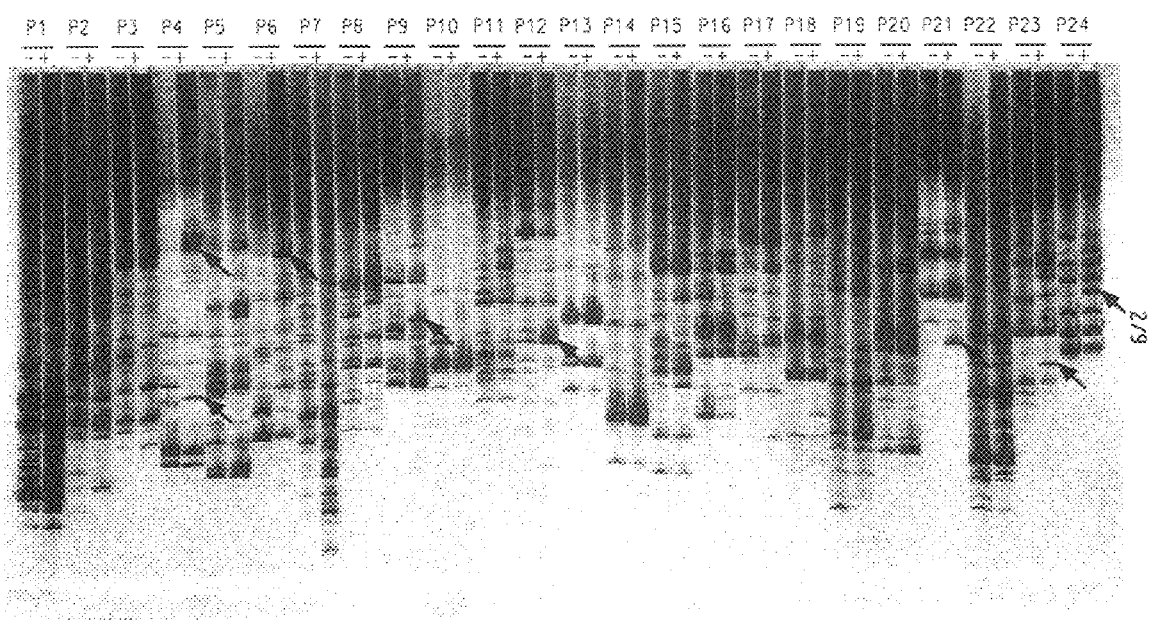

FIG. 2 is a photography of examples of differentially expressed bands on a high resolution precast, silver stained polyacrylamide gel.

Figure 3:
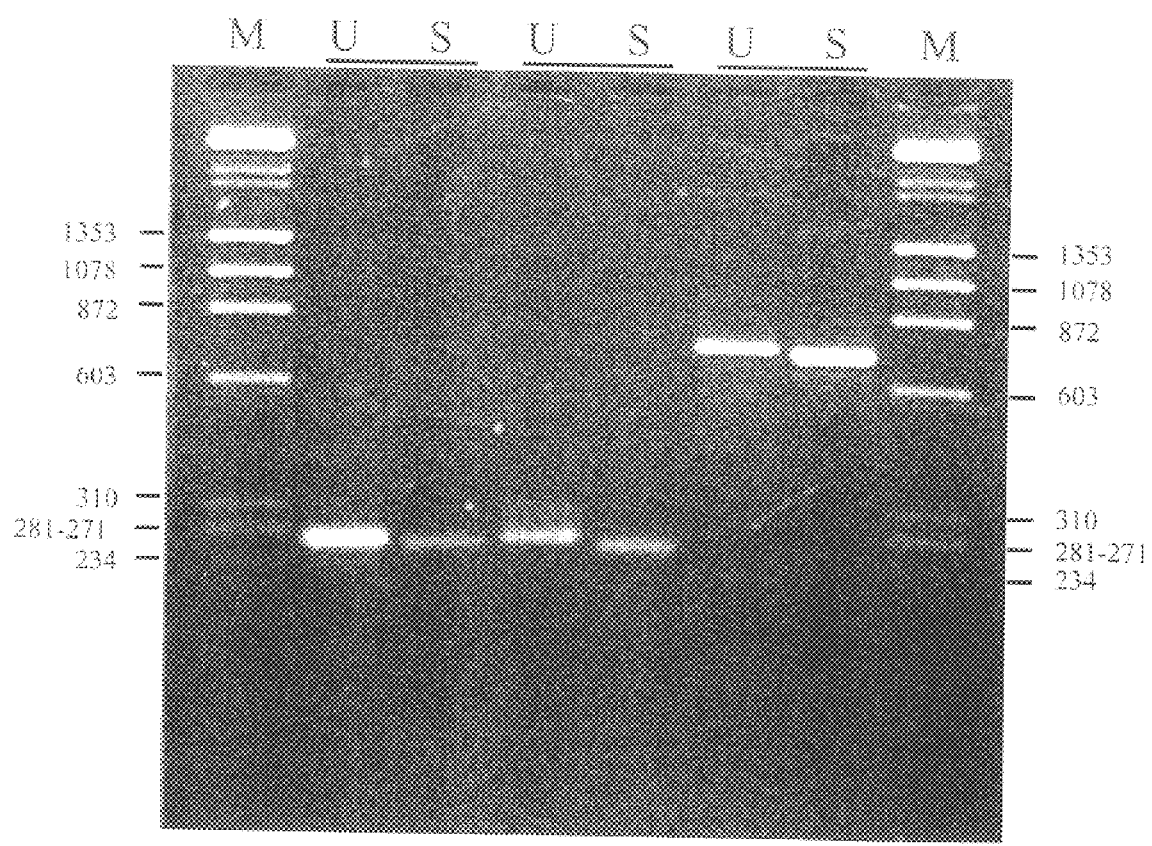

FIG. 3 presents the DNA bands reamplified from the DNA eluted from excised RT-PCR bands off of silver stained polyacrylamide gel. The reamplified bands are analyzed on agarose gel and stained with ethidium bromide.

Figure 4:
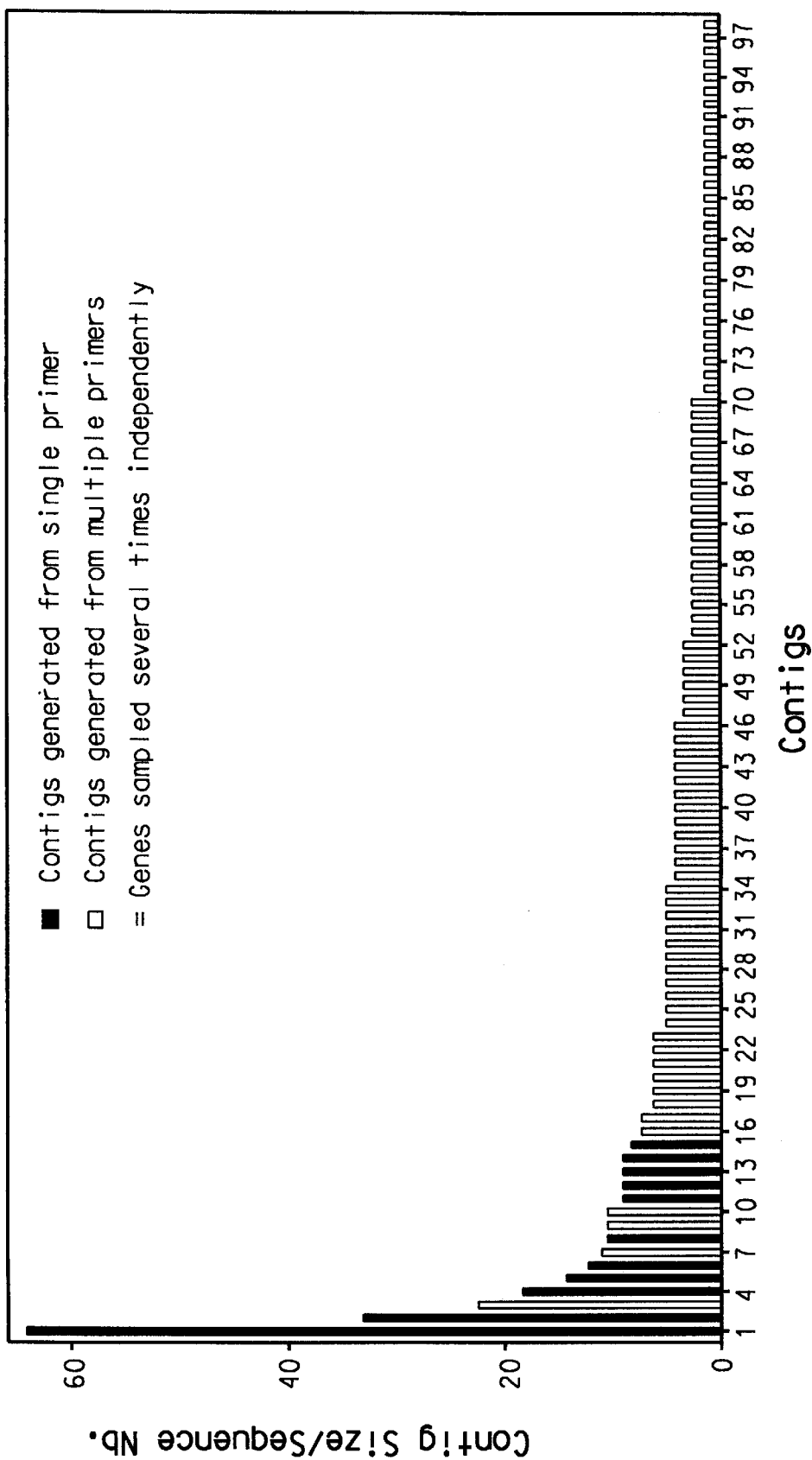

FIG. 4 presents a diagram showing the distribution of DNA sequences assembled in each contig.

Figure 5:
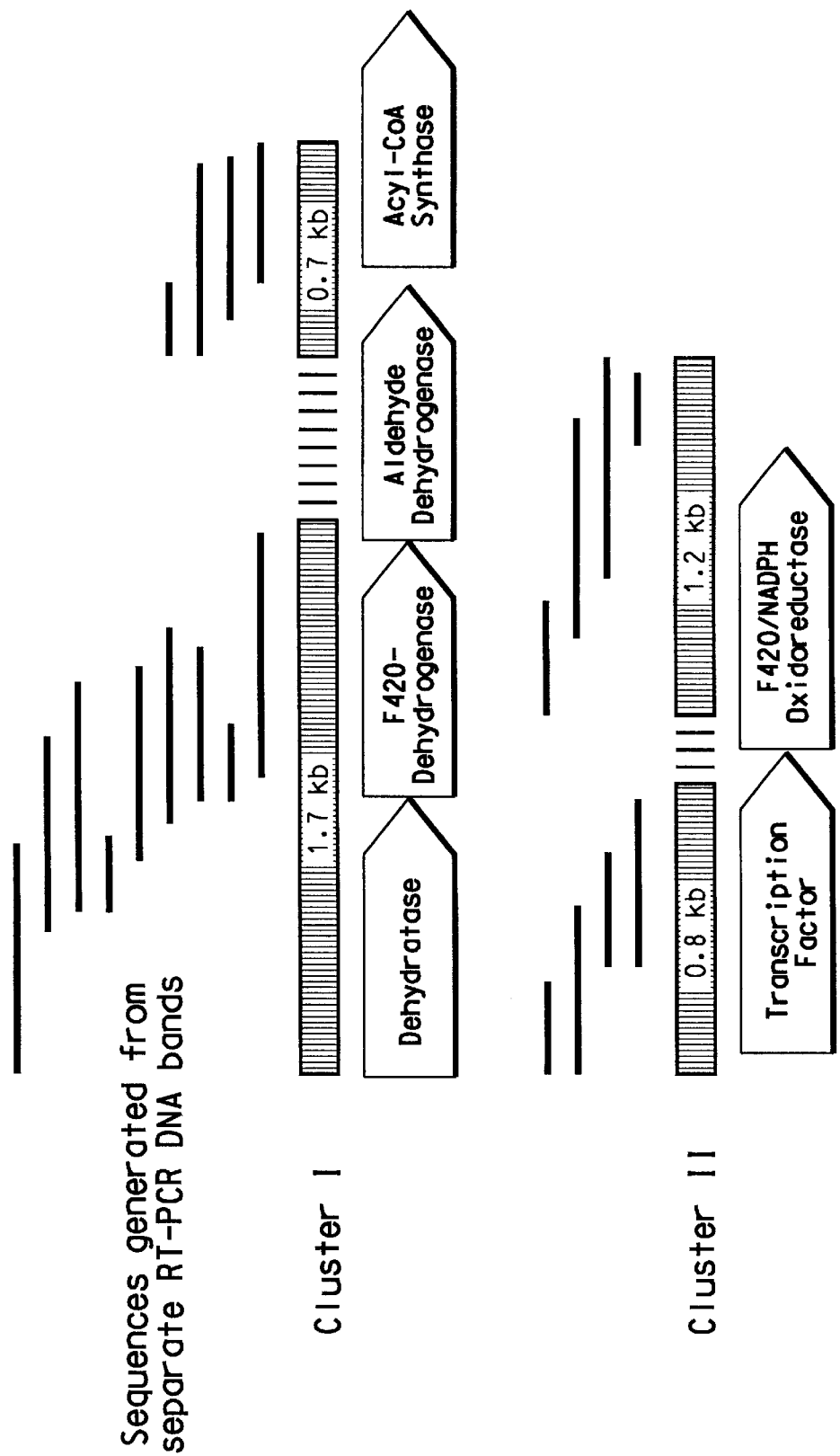

FIG. 5 presents a diagram showing the contig assembly from the sequences encoding picric acid degradation genes of differentially expressed bands.

Figure 6:
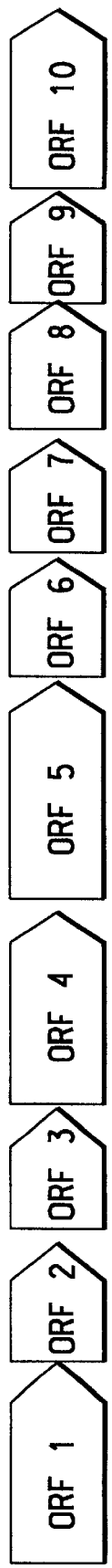

FIG. 6 presents a diagram showing organization of the gene cluster involved in picric acid degradation, isolated from R. erythropolis HL PM-1.

Figure 7:
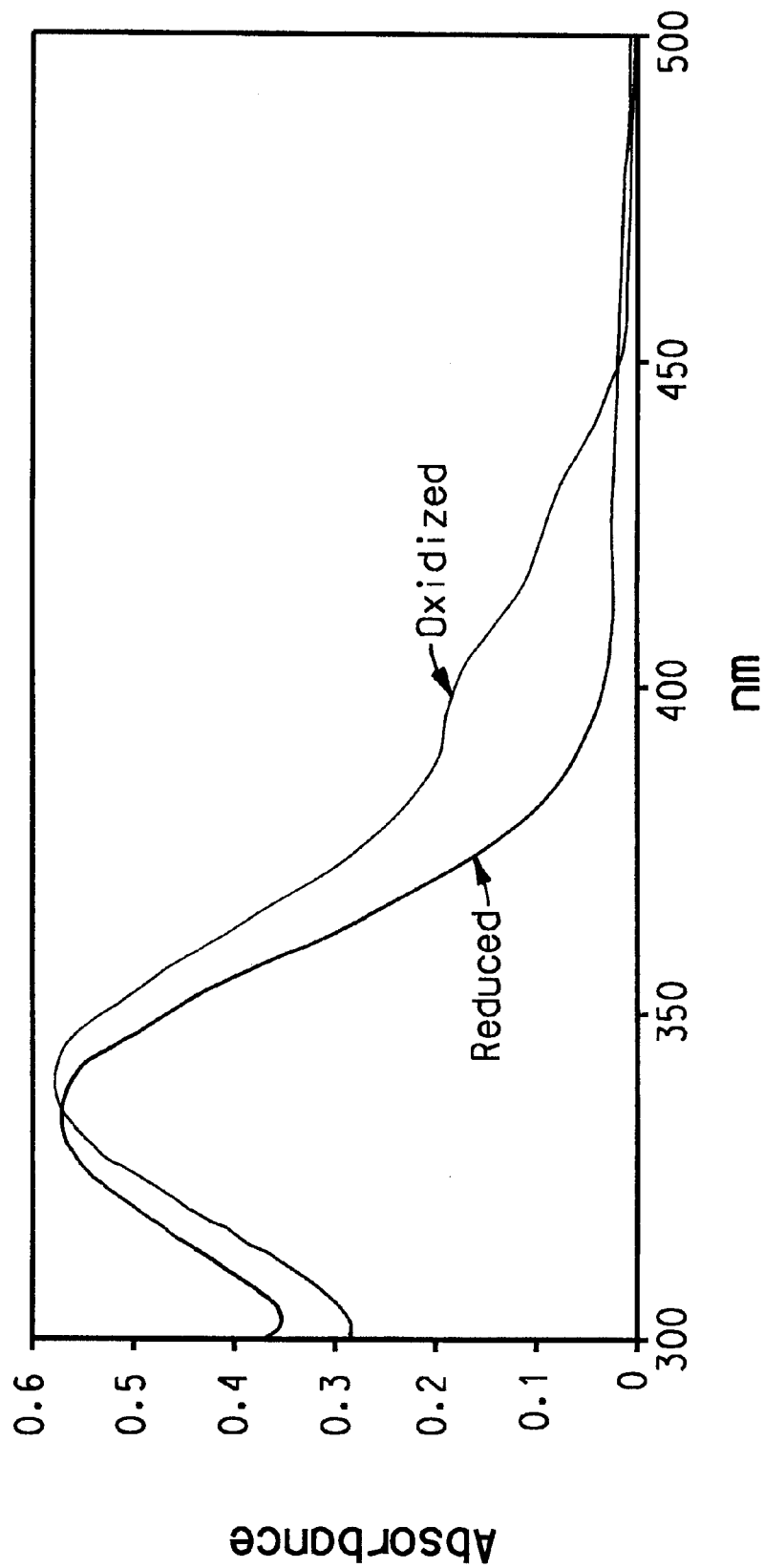

FIG. 7 presents a diagram showing the activity of the cloned F420/NADPH oxidoreductase (ORF7).

Figure 8A:
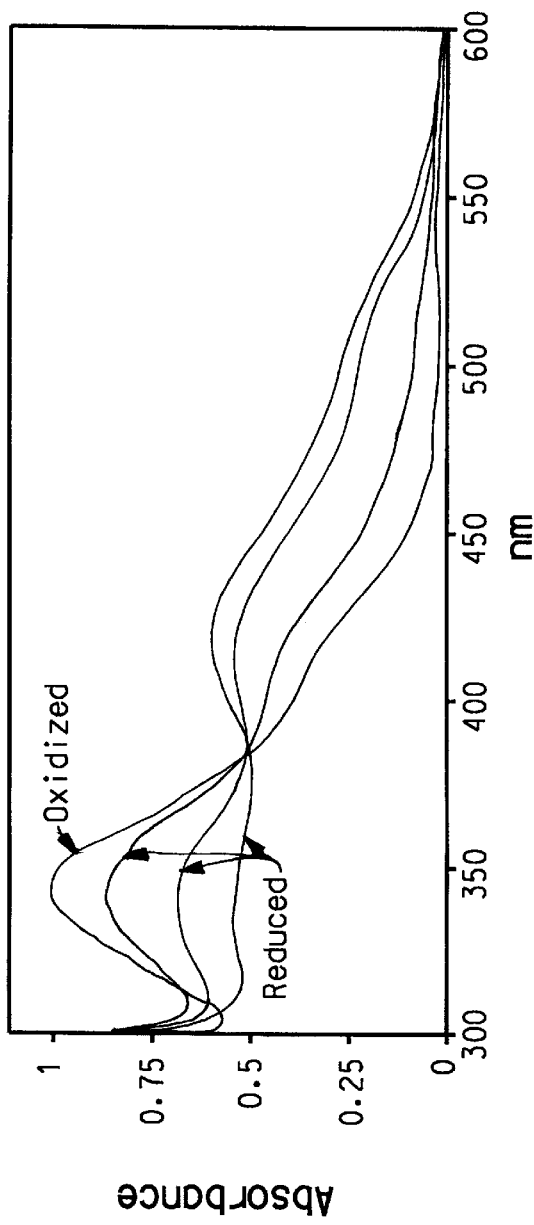

FIG. 8A presents a diagram showing the reduction of picric acid by E. coli cell extracts expressing the picric acid/DNP F420-dependent dehydrogenase (ORF8).

Figure 8B:
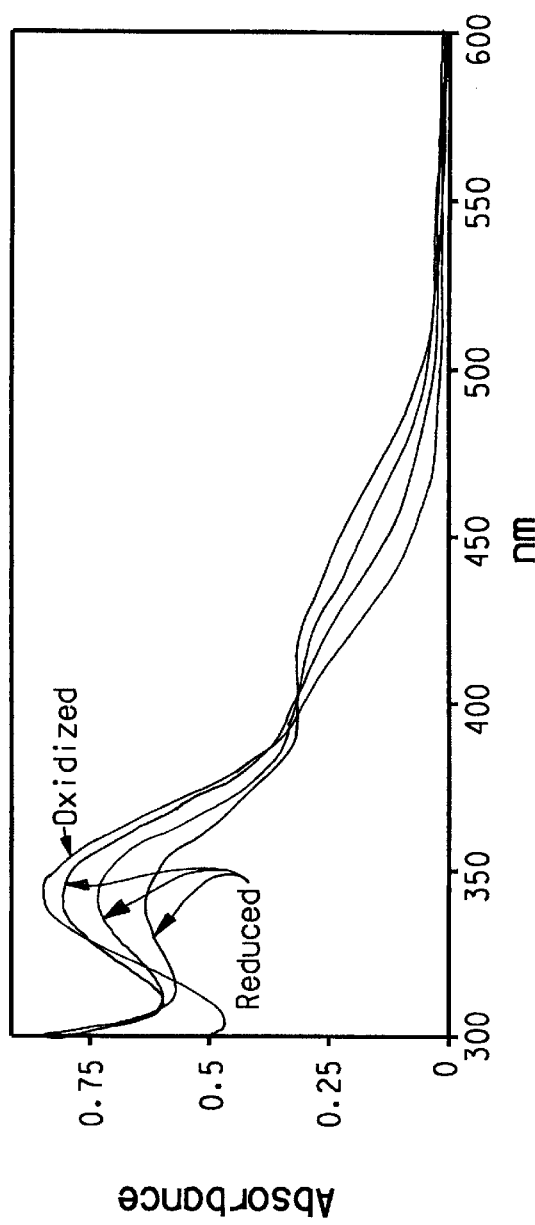

FIG. 8B presents a diagram showing the reduction of dinitrophenol by E. coli cell extracts expression the picric acid/DNP F420-dependent dehydrogenase (ORF8).

Figure 9:
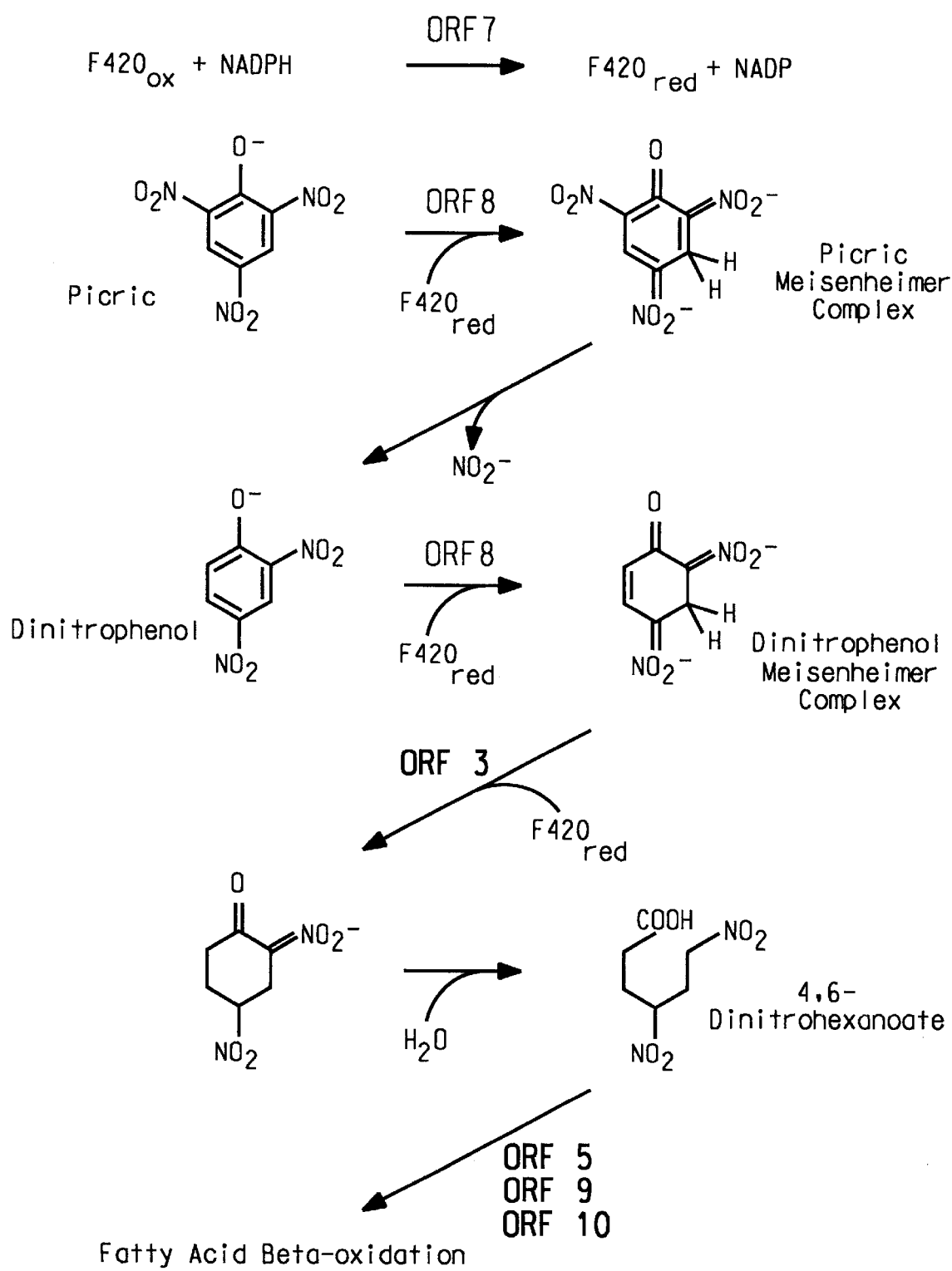

FIG. 9 presents a diagram showing a proposed pathway for the degradation of picric acid and dinitrophenol and an assignment of biochemical functions for the enzymes encoded by the ORFs of the picric degradation gene cluster.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST2.5 (1998) and the sequence listing requirements of the EPO and PCT (Rules 5.2 and 49.5(a-bis), and Section 208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13:3021–3030 (1985) and in the *Biochemical Journal* 219:345–373 (1984) which are herein incorporated by reference.

SEQ ID NO:1 is the nucleotide sequence of the 12.5 kb picric acid degradation gene cluster from identified from *Rhodococcus erythropolis* HL PM-1 by high density sampling mRNA differential display in Example 1.

SEQ ID NO:2 is the partial nucleotide sequence of ORF1 of the picric acid degradation gene cluster from *Rhodococcus erythropolis* HL PM-1 encoding for a transcription factor.

SEQ ID NO:3 is the deduced amino acid sequence of ORF1 encoded by SEQ ID NO:2.

SEQ ID NO:4 is the nucleotide sequence of ORF2 of the picric acid degradation gene cluster from *Rhodococcus erythropolis* HL PM-1 encoding a dehydratase.

SEQ ID NO:5 is the deduced amino acid sequence of ORF2 encoded by SEQID NO:4.

SEQ ID NO:6 is the nucleotide sequence of ORF3 of the picric acid degradation gene cluster from *Rhodococcus erythropolis* HL PM-1 encoding an F420-dependent dehydrogenase.

SEQ ID NO:7 is the deduced amino acid sequence of ORF3 encoded by SEQ ID NO:6.

SEQ ID NO:8 is the nucleotide sequence of ORF4 of the picric acid degradation gene cluster from *Rhodococcus erythropolis* HL PM-1 encoding an aldehyde dehydrogenase.

SEQ ID NO:9 is the deduced amino acid sequence of ORF4 encoded by SEQ ID NO:8.

SEQ ID NO:10 is the nucleotide sequence of ORF5 of the picric acid degradation gene cluster from *Rhodococcus erythropolis* HL PM-1 encoding an Acyl-CoA Synthase.

SEQ ID NO:11 is the deduced amino acid sequence of ORF5 encoded by SEQ ID NO:10.

SEQ ID NO:12 is the nucleotide sequence of ORF6 of the picric acid degradation gene cluster from *Rhodococcus erythropolis* HL PM-1 encoding a Transcription regulator.

SEQ ID NO:13 is the deduced amino acid sequence of ORF6 encoded by SEQID NO:12.

SEQ ID NO:14 is the nucleotide sequence of ORF7 of the picric acid degradation gene cluster from *Rhodococcus erythropolis* HL PM-1 encoding an F420/NADPH oxidoreductase.

SEQ ID NO:15 is the deduced amino acid sequence of ORF7 encoded by SEQID NO:14.

SEQ ID NO:16 is the nucleotide sequence of ORF8 of the picric acid degradation gene cluster from *Rhodococcus erythropolis* HL PM-1 encoding an F420-dependent picric/DNP reductase.

SEQ ID NO:17 is the deduced amino acid sequence of ORF8 encoded by SEQ ID NO:16.

SEQ ID NO:18 is the nucleotide sequence of ORF9 of the picric acid degradation gene cluster from *Rhodococcus erythropolis* HL PM-1 encoding an Enoyl-CoA dehydratase.

SEQ ID NO:19 is the deduced amino acid sequence of ORF9 encoded by SEQ ID NO:18.

SEQ ID NO:20 is the nucleotide sequence of ORF10 of the picric acid degradation gene cluster from *Rhodococcus erythropolis* HL PM-1 encoding an Acyl-CoA dehydrogenase. This sequence is a partial sequence covering the first 1074 nucleotides of the gene.

SEQ ID NO:21 is the deduced amino acid sequence of ORF10 encoded by SEQ ID NO:20. This sequence is a partial sequence covering the first 361 amino acids of the protein.

SEQ ID NO:22 is the sequence of the primers used in this study 5'-CGGAGCAGATCGVVVVV-3' where V represents all the combinations of the three bases A, G and C at the last five positions of the 3' end.

SEQ ID NO:23 is the sequence of the universal primer used for the reamplification of the differentially amplified bands 5'-AGTCCACGGAGCATATCG-3'.

SEQ ID NO:24 is the sequence of the common region of the 240 primers used in this invention 5'-CGGAGCAGATCG-3'.

SEQ ID NO:25, SEQ ID NO:26, SEQ ID NO:27, SEQ ID NO:28, SEQ ID NO:29, SEQ ID NO:32, SEQ ID NO:33, SEQ ID NO:34, and SEQ ID NO:37 are the amino acid sequences of cyclohexanone monooxygenases identified by performing differential display on a microbial enrichment.

SEQ ID NO:30 is the partial amino acid sequence of a succinic semialdehyde dehydrogenase identified by performing differential display on a microbial enrichment.

SEQ ID NO:31 is the partial amino acid sequences of an acetylphosphinothricin-tripetide-deacetylase identified by performing differential display on a microbial enrichment.

SEQ ID NO:35 is the partial amino acid sequence of a transcriptional regulator identified by performing differential display on a microbial enrichment.

SEQ ID NO:35 and 36 are partial amino acid sequences of a transcriptional regulator identified by performing differential display on a microbial enrichment.

DETAILED DESCRIPTION OF THE INVENTION

The present invention provides a new technique that has been developed which uses arbitrarily primed RT-PCR amplification of DNA fragments from subsets of total RNA population to detect cDNA fragments from differentially expressed mRNAs. The technique involves a high density sampling of mRNA population using a large set of PCR primers. The induced genes are independently sampled multiple times and the short, randomly amplified DNA fragments generated can then be assembled into large contiguous sequences. These contiguous sequences carry the complete gene of interest as well as link contiguous genes which are part of an operon.

In one embodiment, and unlike previously known differential display methods, the claimed invention generates reliable assembled contigs from sequences generated from more than one primer and permits a facile approach to discover novel genes in any microbe by mRNA differential display.

In a preferred embodiment, the complete procedure embodies integrated simple protocols in a streamlined process that uses a single primer per RT-PCR reaction, a "single tube" RT-PCR reaction, a 96 well format, and thus lends itself to automated pipetting by a robot. For facile separation of the RT-PCR DNA fragments, flat bed precast polyacrylamide gels may be used which make the method of the present invention amenable to automation and silver staining. The combination of the elements of these preferred embodiments results in a simplified and highly reproducible method for the identification and assembly of complex genetic elements.

In the application, unless specifically stated otherwise, the following abbreviations and definitions apply:

"Open reading frame" is abbreviated ORF.

"Polymerase chain reaction" is abbreviated PCR.

"Reverse transcription followed by polymerase chain reaction" is abbreviated RT-PCR.

"Random amplification of polymorphic DNA" is abbreviated RAPD.

"Dinitrophenol" is abbreviated DNP.

"RAPD patterns" refer to patterns of arbitrarily amplified DNA fragments separated by electrophoresis.

"Universal reamplification primer" refers to a primer including at its 3' end the nucleotide sequence common to 5' end of all arbitrary primers of the present invention.

"Specific primer" refers to the arbitrary primer originally used in an RT-PCR reaction to generate a differentially amplified RAPD DNA fragment and which is then subsequently used for the reamplification of same RAPD bands eluted from the polyacrylamide gel.

"Universal primer" refers to a primer that includes at its 3' end a sequence common to the 5' end of all arbitrary primers of the collection and which can thus be used to reamplify by PCR any DNA fragment originally amplified by any arbitrary primer of the primer collection.

The term "differential display" will be abbreviated "DD" and refers to a technique in which mRNA species expressed by a cell population are reverse transcribed and then amplified by many separate polymerase chain reactions (PCR).

PCR primers and conditions are chosen so that any given reaction yields a limited number of amplified cDNA fragments, permitting their visualization as discrete bands following gel electrophoresis or other detection techniques.

The term "primer" refers to an oligonucleotide (synthetic or occurring naturally), which is capable of acting as a point of initiation of nucleic acid synthesis or replication along a complementary strand when placed under conditions in which synthesis of a complementary stand is catalyzed by a polymerase. Wherein the primer contains a sequence complementary to a region in one strand of a target nucleic acid sequence and primes the synthesis of a complementary strand, and a second primer contains a sequence complementary to a region in a second strand of the target nucleic acid and primes the synthesis of complementary strand; wherein each primer is selected to hybridize to its complementary sequence, 5' to any detection probe that will anneal to the same strand.

A primer is called "arbitrary" in that it can be used to initiate the enzymatic copying of a nucleic acid by a reverse transcriptase or a DNA polymerase even when its nucleotide sequence does not complement exactly that of the nucleic acid to be copied. It is sufficient that only part of the sequence, in particular the 5 to 8 nucleotides at the 3' end of the molecule, hybridizes with the nucleic acid to be copied. For that reason no sequence information of the template nucleic acid need be known to design the primer. The sequence of the primer can be designed randomly or systematically as described in this invention. "Arbitrary primers" of the present invention are used in a collection so that there are at least 32 primers in a collection. Each of the arbitrary primers comprise a "common region" and a "variable region". The term "common region" as applied to an arbitrary primer means that region of the primer sequence that is common to all the primers used in the collection. The term "variable region" as applied to an arbitrary primer refers to a 3' region of the primer sequence that is randomly generated. Each of the primers in a given collection is unique from another primer, where the difference between the primers is determined by the variable region.

As used herein "low stringency" in referring to a PCR reaction will mean that the annealing temperature of the reaction is from about 30° C. to about 40° C. where 37° C. is preferred.

The term "complementary" is used to describe the relationship between nucleotide bases that are capable of hybridizing to one another. For example, with respect to DNA, adenosine is complementary to thymine and cytosine is complementary to guanine.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism.

As used herein the term "differentially expressed gene" refers to a gene, the transcription of which is modulated in response to some stimulus or "stimulating agent". The "stimulating agent" may serve to increase or up-regulate transcription of the gene, in which case the stimulating agent is an "inducing agent". Where the stimulating agent serves to decrease or down-regulate gene transcription the stimulating agent is an "inhibiting agent". The "inducing agent" or "inhibiting agent" may comprise any substance or condition that produces an alteration in the transcription of a "differentially expressed gene".

"Coding sequence" refers to a DNA sequence that codes for a specific amino acid sequence.

"Contig" refers to a group of DNA sequences with overlapping segments forming one larger continuous sequence.

As used herein the term "population of cells" means a collection of microbial cells. The collection may be a pure culture, or may be a mixed or enriched culture or a consortium. Microbial cells particularly amenable to the method of the present invention include but are not limited to prokaryotic cells such as bacteria and archaebacteria as well as fungi, yeasts.

The term "amplify" or "amplification" is the process in which a complementary copy of a nucleic acid strand, (DNA or RNA) is synthesized by a polymerase enzyme and the synthesis is repeated in cyclical manner such that the number of copies of the nucleic acid is increased in either a linear or logarithmic fashion. A variety of nucleic acid amplification methods are known in the art including thermocycling methods such as polymerase chain reaction (PCR) and ligase chain reaction (LCR) as well as isothermal methods and strand displacement amplification (SDA). Additional methods of RNA replication such as replicative RNA system (Qβ-replicase) and DNA dependent RNA-polymerase promoter systems (T7 RNA polymerase) are contemplated to be within the scope of the present invention.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present method of differential display by high density sampling of prokaryotic mRNA may be viewed as having seven general steps: 1) growth and induction of cultures, 2) total RNA extraction, 3) primer and primer plate design, 4) arbitrarily primed reverse transcription and PCR amplification, 5) elution, reamplification and cloning of differentially expressed DNA fragments, 6) assembly of clones in contigs and sequence analysis and 7) identification of induced metabolic pathways.

Culture Growth:

The initial phase of the present method involves the culturing and induction or inhibition of cultures. Typically, a bacterial culture is grown under non-stimulated conditions. It is then split in two cultures one of which is treated for the appropriate time to induce the biochemical pathway or the physiological response of interest. The non-treated culture is used as a control in all the experiments.

It will be appreciated that the present method may also have application in the analysis of the difference between different related populations of cells. For example, genotypic differences between wildtype and mutant strains or benign and pathogenic strains may be analyzed by the present method. A variety of microbes are amenable to analysis by the present method including, but not limited to, bacteria, archaebacteria yeasts and filimentus fungi, where bacteria are particularly suitable. It will be appreciated that, since the present method does not rely on the knowledge of any particular sequence, it is not limited to the analysis of pure cultures, but is equally applicable to mixed cultures of organisms such as consortia. Isolation of genes from consortia make possible the identification of complete pathways, only parts of which may be present in any given organism of the consortium.

In addition, the method of the invention could be employed to examine the inhibitory effects of various treatments on mRNA levels. In this case the steady-state mRNA levels encoding certain gene/s would be decreased upon treatment.

In all instances where induction or inhibition is used, inducing or inhibiting conditions require that the culture be contacted with an inducing or inhibiting agent of some kind. This agent may be a variety of chemicals or conditions that result in change in the transcription of at least one gene in the cells of the culture. These agents may include but are not limited to chemicals, environmental pollutants, heavy metals, changes in temperature, changes in pH as well as agents producing oxidative damage, DNA damage, anaerobiosis, changes in nitrate availability or pathogenesis. The effect of these treatments on mRNA levels can be compared to the changes in catalytic activities of selected enzymes.

In one application the present method was validated using cultures of *Rhodococcus erythropolis* strain HL PM-1, where the cultures were induced in the presence of picric acid or dinitrophenol (DNP), to determine the genes involved in picric acid degradation.

Total RNA Extraction:

As the method relies on an analysis of differentially expressed RNA, total RNA from the cultures must be extracted. Methods of RNA extraction are common and well known in the art (see for example Speirs, et al., *Methods Plant Biochem.* (1993), 10 (Molecular Biology), 1–32; Maniatis, supra). Preferred in the present invention is a method involving total RNA extraction by rapid centrifugation of chilled cultures and disrupting the cell pellet in a bead beater by zirconia/silica beads in the presence of a chemical agent denaturing RNases such as acid phenol or guanidium isothiocyanate. It will be appreciated by the skilled person that these, or similar steps, are important in order to avoid message degradation. Prokaryotic mRNA lack stabilizing poly-A tails and are rich in RNases, resulting in much shorter mRNA half life (minutes) compared to eukaryotic mRNA (hours). The RNA preparation is then treated with RNase free DNase to remove traces of DNA that might complicate RT-PCR reaction by serving as a template in the amplification step. The RNA must be tested for absence of DNA contamination by showing that the generation of randomly amplified DNA fragments using the RNA preparation as a template requires the presence of a reverse transcriptase. This RNA extraction method usually yields sufficient RNA (stable RNA (tRNA and rRNA)+messenger RNA) from 10 mL culture to perform the 240 RT-PCR reactions of a complete experiment.

Primer and Primer Plate Design:

The present invention uses a large collection of primers, comprising a 5' common region and a 3' variable region. Arbitrary primers of the present invention may be of any length appropriate for priming where a length of about 10 to 50 bases is recommended and a length of about 10 to about 20 bases is preferred. Within any given set of primers there is only one common region and all variation in the primer collection is generated by the variable region. Within any given primer collection no two primers are identical, each having a different sequence at the variable region. The variable region of the primer in the collection is located at the 3' end of the primer and may be from about 4 to about 8 bases in length. Collections will contain at least 32 primers, where collections of 80 to 500 unique primers are suitable and sets of 100 to 250 primers are preferred.

The primers used herein are a collection of 240 primers according to the sequence 5'-CGGAGCAGATCGVVVVV-3' (SEQ ID NO:22) where VVVVV (variable region) represents all the combinations of the three bases A, G and C at the last five positions of the 3'-end, and CGGAGCAGATCG (SEQ ID NO:24) represents the common region. The 240 primers correspond to the 243 possibilities of A, G, or C at the 3' end minus the three primers ending with the sequences GCCGGC, GGCGCC and GGGCCC which form the strongest primer dimers and lead to unproductive RT-PCR reactions. Larger primer sets may also be designed that would include for example all of A, C and G possibilities at the first four V positions and A, G, C, and T at the last V position, or all the ACG at the last six 3' end positions. Such larger sets would serve to increase the density of sampling of the mRNA population.

The 5' end sequence common to all primers in the set was designed to minimize homology towards both orientations of the 16S rDNA sequences and thus further minimize non specific amplification of these abundant and stable RNA species. This was done by testing the predicted primability of random sequences to the nucleotide sequences of the 16S genes from various prokaryotes using the "electronic PCR" program Amplify (University of Wisconsin/Genetics department) with parameters of 80% primability and 40% stability and discarding sequences that formed even poor predicted base pairing. The common sequence used in the primer set was originally designed to limit hybridization with mostly Archaeal 16S sequences. The 16S genes screened were those of *Actinomyces bovis, Archaeoglobus fulgidus, Bacillus subtilis, Bacteroides thelaiotaomicrons, Chloroflexus aurantus, Escherichia coli, Halobacillus litoralis, Halobacterium halobium, Halococcus morrhuae, Marinobacter hydrocarbonoclasticus, Methanobacterium thermoautotrophicum, Pyrodictium occultum, Sulfolobus solfataricus, Thermofilum pendens, Thermotoga maritima*. Other 5' end common sequence designed to bias the RT-PCR amplification against stable RNAs could be designed for the absence of homology to (1) both the 16S rDNA as well as the 23S rDNA genes and (2) for a wider range of prokaryotes with more widespread phylogenetic position.

The 5' end sequence common to all primers (5'-CGGAGCAGATCG - - - ) (SEQ ID NO:24) also allows the reamplification of all differentially amplified bands with a single primer (5'-AGTCCA<u>CGGAGCATATCG</u>-3', SEQ ID NO:23) that include this sequence (underlined) at its 3' end. For each band, the reamplification is performed with the "specific" primer, i.e., the primer of the collection that generated the band in the specific RT-PCR reaction. The reamplification can also be performed as well as with a "universal" primer that includes the 12 nucleotide sequences common to all the arbitrary primers. Variations in the design of this common tail may include a longer common sequence, for example 20 nucleotides, to allow for greater stringency in the PCR reamplification.

At low stringency, the annealing of the primer to the template RNA or DNA and the initiation of DNA polymerization are determined by the last 5 to 7 bases at the 3' end. The 10–12 nucleotide at the 5' end are selected in a way that they serve to stabilize the base pairing with the template. The common sequence presented above with 8 C/G and 4 A/T (67% C/G) was designed to be used with bacteria with high G+C content. A similar oligonucleotide set with 4 C/G and 8 A/T (33% C/G) can be designed to be used with low G+C content organisms.

Other preferred variations in the design of the large primer set might include: different methods of labeling oligonucleotides (e.g., fluorescent or biotinylated) for visualizing DNA fragments in the gel; sequence targeting the nucleotide sequence coding for conserved protein domains such as nucleotide binding domains or ribosome binding sites in order to bias the sampling toward specific genes or coding region; inclusion of restriction sites for further cloning of the fragment; inclusion of the restriction sites for excision of the primer from the sequence amplified; or inclusion of any other specific nucleotide sequence for molecular biology and genetic manipulations relating to the labeling, the fusion or the expression of the DNA sequence amplified.

Because a large set of primers are used, reactions may be assembled in a 96 well microtiter format. Many sets of 5 plates may be prepared at one time, with primers aliquoted manually or with automation, and stored in a freezer for subsequent use.

An example of an array of primers on 96 well plates is prepared as follows. The 240 primers are pre-aliquoted on five 96 well PCR plates. In each plate, 4 µL of each primer (2.5 µM) is placed in two adjacent positions as indicated below.

| Plate #1 contains primers number A1 to A48 | | | | | | | | | | | |
|---|---|---|---|---|---|---|---|---|---|---|---|
| A1 | A1 | A2 | A2 | A3 | A3 | A4 | A4 | A5 | A5 | A6 | A6 |
| A7 | A7 | A8 | A8 | A9 | A9 | A10 | A10 | A11 | A11 | A12 | A12 |
| A13 | A13 | A14 | A14 | A15 | A15 | A16 | A16 | A17 | A17 | A18 | A18 |
| A19 | A19 | A20 | A20 | A21 | A21 | A22 | A22 | A23 | A23 | A24 | A24 |
| A25 | A25 | A26 | A26 | A27 | A27 | A28 | A28 | A29 | A29 | A30 | A30 |
| A31 | A31 | A32 | A32 | A33 | A33 | A34 | A34 | A35 | A35 | A36 | A36 |
| A37 | A37 | A38 | A38 | A39 | A39 | A40 | A40 | A41 | A41 | A42 | A42 |
| A43 | A43 | A44 | A44 | A45 | A45 | A46 | A46 | A47 | A47 | A48 | A48 |

The ordering of the primers on the plates corresponds to the order of the systematic sequence variations in the design of the 3' end of the sequence CGGAGCAGATCGVVVVV (SEQ ID NO:22) (where VVVVV represents all the combinations of the three bases A, G and C at the last five positions of the 3' end) as shown below:

VVVVV is AAAAA in primer A1

VVVVV is AAAAC in primer A2

VVVVV is AAAAG in primer A3

VVVVV is AAACA in primer A4

VVVVV is AAACC in primer A5

VVVVV is AAACG in primer A6

VVVVV is AAAGA in primer A7

VVVVV is AAAGC in primer A8

VVVVV is AAAGG in primer A9

VVVVV is AACAA in primer A10 etc.

Ordering of the primers on the plates can be variable. Using the algorithm of Breslauer et al. (*Proc. Natl. Acad. Sci. USA* 83:3746–3750 (1986)) the Tm of the primers in the collection can be calculated to vary from 55.4° C. for the primer where VVVVV is AAAAA to 67.5° C. for the primer where VVVVV is GGGGG. The 240 primers may be ranked by increasing Tm and separated into five 96-well plates, each corresponding to a narrower Tm interval. This will allow the optimization of the annealing temperature of the two low stringency reactions for individual primer plates.

PCR products from control and induced RNA generated from the same primers are analyzed side by side by staining the gel using, for example Plus One DNA silver staining kit (Amersham Pharmacia Biotech Piscataway, N.J.). The total analysis was completed within only two hours of the RT-PCR reaction.

Arbitrarily Primed Reverse Transcription and PCR Amplification:

The present method utilizes a large number of arbitrary primers, designed as described above, for the multiple sampling of the extracted RNA. Unlike published methods, the increased number of arbitrary primers confers on the present method the ability to differentiate between genetically different cell populations with a very low incidence of false positives. Increasing the number of arbitrary primers used has the added advantage of requiring a relatively low resolution separation system. This adds to the speed and cost effectiveness of the method.

In a preferred embodiment the arbitrarily primed reverse transcription (RT) and the PCR amplification may be performed in a single tube. This embodiment may be effected using commercially available RT kits such as those supplied by from Gibco-BRL (Superscript One-Step RT-PCR System). These kits provide the reverse transcriptase, and the Taq polymerase and a buffer system compatible with both reactions in a single tube, as well as other reagents necessary for priming and amplification. Advantages of the single tube approach include a reduction in experimental variability and increased reproducibility.

Amplification protocols using the present arbitrary primers are common and well known in the art. Preferred in the present invention are PCR-type amplification methods, employing for example reagents containing, nucleotide triphosphates, at least one primer with appropriate sequence (s), DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.).

Typical PCR procedures employs a thermocycling protocol which consists of a melting step to separate the complementary strands of DNA; a primer annealing step to allow hybridization of the primers to the single stranded DNA (ssDNA) and initiation of polymerization; and a primer extension step to complete the copy initiated during annealing. This final extension step allows polymerization to complete all strands. In the present invention the thermocyling procedure will be repeated from 1 to 50 times depending on the need for amplification and the stability of the reagents. The variables of number of cycles, denaturation and annealing temperatures as well as the length of time in each phase of the thermocycling process would affect the specificity, sensitivity, efficiency, reproducibility and fidelity. A typical thermocycling procedure will call for a 5 minutes denaturation step at 94° C. followed by an annealing step of 2 minutes at 50° C. and concluding with a polymerization step of 3 minutes at 72° C. As will be appreciated by the skilled person, amplification is more efficient if annealing is carried out at lower temperature (i.e., 37° C.), however mis-priming is a common occurrence at this temperature. On the other hand, at higher temperature of about 55° C. for example the efficiency of amplification is reduced, although the specificity is higher. The skilled person will know how to manipulate these variables within the context of the present invention to achieve the desired result.

As applied to the present invention it is preferred if the PCR reactions using the arbitrary primers are at low stringency. As used herein low stringency in referring to a PCR reaction will mean that the annealing temperature of the reaction is from about 30° C. to about 40° C. where about 37° C. is preferred. Additionally it is preferred if the number of cycles is less than 20.

Elution, Reamplification and Cloning of Differentially Expressed DNA Fragments:

Methods of separating PCR amplification products are common and well known in the art. Typically electrophoresis on agarose gels may be used, although methods of HPLC separation and capillary electrophoresis have also been utilized (Wages et al., *High Performance Liquid Chromatograph: Princ. Methods Biotechnol.* (1996), 351–379. Editor (s): Katz, Elena D. Publisher: Wiley, Chichester, UK.; Righetti et al., *Forensic Sci. Int.* (1998), 92(2–3), 239–250).

Where gel electrophoresis is used, commercially available pre-cast polyacrylamide urea gels are preferred for ease of handling and speed. Although a variety of methods for visualizing nucleic acids on gels is known (including intercalating dyes such as ethidium bromide and others [see for example, U.S. Pat. No. 5,563,037; U.S. Pat. No. 5,534,416; U.S. Pat. No. 5,321,130] and radioactivity) the preferred method of visualizing in the present invention is the use of silver stain (Doss, (1996) *Biotechniques* 21 (3):408–412, Lohmann, et al., (1995) *Biotechniques* 18 (2):200–202, Weaver, et al., (1994) *Biotechniques* 16 (2):226–227, Men and Gresshoff, (1998) *Biotechniques* 24 (4):593–595).

After silver staining the gel band of interest is excised and soaked in a small volume (20–50 $\mu$L) of an elution solution containing, a dilute sodium cyanide (approximately 5 to 20 mM) to resolubilize the metallic silver precipitated over the DNA, a mild detergent such as nonyl phenoxy polyethoxy ethanol (NP-40) or Triton X-100 (0.5–0.005%) and a salt such as KCl to facilitate the diffusion of the DNA out of the polyacrylamide in a buffer at pH~8 compatible with the subsequent PCR reaction and the stability of cyanide in solution. The DNA is then allowed to diffuse out of the polyacrylamide by incubation at 95° C. for about 20 minutes.

The silver stain consists of a precipitate of metallic silver over the DNA molecules, which forms a coating that restricts the elution of the DNA from the gel. Therefore a large number of PCR cycles or rounds of reamplification would compensate for a inefficient elution of the DNA from the polyacrylamide. On the other hand, the probability of amplification of background DNA, i.e., the reamplification of the DNA sequence which is not that of the differential amplified RT-PCR DNA band, would contribute to the generation of false positives in the differential display experiment. It is thus preferred to keep the number of reamplification PCR cycles as low as possible (<20) in order to reamplify the correct DNA species. Routine reamplification of the DNA eluted from the silver stained gel with less than 20 PCR cycles is made possible with the use of the sodium cyanide in the elution solution.

Next, an aliquot of the elution solution prepared above is used as the template in a new PCR reaction. This PCR reaction includes either the common reamplification primer or the arbitrary primer which had generated the band in the RT-PCR reaction.

Each reamplified fragment is then cloned into an appropriate cloning vector such as the blue/white cloning vector pCR2.1-Topo (Invitrogen), for example. Since all the DNA fragments amplified in a single RT-PCR reaction incorporate the same ends, the background smear of DNA present in the excised slice of polyacrylamide gel containing the differentially amplified band can also be cloned. Four to eight clones from the cloning of each differentially expressed band were then submitted to sequencing using the "universal" forward sequencing primer. Inserts that were not completely sequenced by this method were sequenced on the other strand with the reverse universal sequencing primer, confirming that the sequence clones correspond to the differentially amplified of the initially identified bands.

Assembly of Clones in Contigs and Sequence Analysis:

The nucleotide sequences obtained were trimmed for vector, primer and low quality sequences, and aligned with an alignment program such as "Sequencher" program (Gene Code Corp., Ann Arbor, Mich.), using default parameters. Two types of contigs were assembled: (i) contigs from several identical sequences corresponding to the multiple clones of a single reamplified band (corresponding to mRNA sampled once by a single RT-PCR reaction) and (ii) longer contig sequences from the sequences of distinct DNA RT-PCR bands.

Generally these bands were generated in separate RT-PCR reactions from distinct primers. Data was analyzed by plotting each contig as shown in FIG. 4. As is seen in FIG. 4, contigs generated in this fashion fall roughly into three groups; those with few numbers of identical sequences (1–3); those with moderate numbers of identical sequences (4–8); and those with a high numbers of identical sequences (9–60). Small number of identical sequences correspond to the sequence of clones of contaminating DNA generated during the reamplification step. This DNA was generated in the same RT-PCR reaction incorporating the same oligonucleotide at its end and is thus reamplified using the same primer. Those contigs containing a moderate (2–4) number of identical sequences are composed sequences from clones obtained the cloning of a reamplified single band, i.e., generated in a single RT-PCR reaction. Confirmation that the genes identified are differentially expressed may easily be determined by dot blot analysis of the RNA, microarray or by Northern blot, or by quantitative RT-PCR analysis. Those contigs comprised of many identical sequences were assembled from multiple distinct, overlapping sequences from clones obtained the cloning of several reamplified bands, i.e., generated in a separate RT-PCR reactions. These correspond to mRNA sampled repeatedly through independent experiments. The multiplicity of sampling strongly suggests that these bands are not false positives and represent truly differentially expressed genes.

Once contigs are assembled, the sequences of the contigs are compared to protein and nucleic acid sequences in databases using an alignment program such as BLAST (Basic Local Alignment Search Tool; Altschul, S. F., et al., (1993) *J. Mol. Biol.* 215:403–410; see also www.ncbi.nlm.nih.gov/BLAST/). Contigs, generated from DNA sequences of bands amplified by distinct primers in independent RT-PCR reactions are statistically less frequent, which strongly suggest that the genes identified are differentially expressed. In the case of abundant metabolic pathways, the multiplicity of sampling can assemble large contigs several kb in length from shorter RT-PCR sequences. These larger contigs may encode complete genes or overlap contiguous genes part of an operon.

As illustrated above, contigs may be assembled by computational means involving a variety of commercially available software systems. Additionally, contigs may be assembled by genetic means. For example, because an RNA message may be sampled multiple times through the generation of differentially amplified RT-PCR bands that do not overlap they can be clustered if their nucleotide or deduced amino acid sequences show homology to different parts of the same gene or protein. In these instances, the physical linkage of the two DNA fragments can be accomplished by PCR amplification from the chromosomal DNA using primers matching the ends of the RT-PCR fragments to link.

Genes Involved in Dinitrophenol and Picric Acid Degradation:

The present invention was used to identify and characterize the genes that are involved in the degradation of dinitrophenol and picric acid (trinitrophenol) in *Rhodococcus erythropolis* strain HL PM-1.

Table 1 and Example 6 lists the contigs assembled from sequences generated from more than one primer. Ten contigs were assembled from bands generated by more than one primer, (2–9 bands). In several instances nested bands were generated from a single primer. Four contigs showed high homology with known genes encoding transcription/translation machinery (16 S rRNA, 23 S rRNA, RNA polymerase). These genes represent the most frequent false positives due to the great abundance of their transcripts and were not pursued further.

Physical linkage between of two of the ten contigs was indicated by the fact that the 3' end of the F420-dependent dehydrogenase contig encoded for the beginning of a gene sharing the homology to an aldehyde dehydrogenase with the 0.7 kb aldehyde dehydrogenase contig (FIG. 5). Two of the assembled contigs carried the genes homologous to that of oxido-reduction enzymes that depend on the unusual redox cofactor deazaflavin F420. Factor F420 has been found in Archaebacteria although its involvement in the metabolism of bacteria (Eubacteria) has only recently been reported, (Purwantini et al., *J. Bacteriol.* 180:2212–2219 (1998); (Peschke et al., *Mol. Microbiol.* 16:1137–1156 (1995)).

FIG. 5 illustrates other ORF's involved in picric acid degradation identified by the present method. For example cluster I shows the assembly of the 3.7 kb F420-dependent oxidoreductase/aldehyde dehydrogenase contig. Cluster II shows the assembly of the 2.7 kb F420/NADPH oxidoreductase/transcription factor contig. Four contigs that were assembled from the DNA sequence of bands generated in independent RT-PCR reactions (Table 1, FIG. 5) were shown to be part of a single large gene cluster that possibly encode for all the genes involved in picric acid degradation (FIG. 6). Two of these genes were cloned in expression vector and expressed in *E. coli*. The first gene encodes for a F420/NADPH oxidoreductase which reduces the deazaflavin F420 with NADPH but not NADH (FIG. 7 and FIG. 9). The second gene encodes for a F420-dependent dehydrogenase which reduces both trinitrophenol (picric) acid and dinitrophenol using reduced F420 as a source of electrons (FIG. 8 and FIG. 9).

Identification of Genes Involved in Cyclohexanone Oxidation:

The present method was also applied to the isolation of genes involved in the oxidation of cyclohexanone from a consortium of bacteria in a manner similar to the technique described above for the isolation of the picric acid degradation pathway. The consortium was isolated by preparing an enrichment culture grown on cyclohexanone as a sole carbon source. Microbiological analysis indicated that the consortium was comprised of Arthrobacter sp., Rhodococcus sp. as well as seven other bacterial species. RNA extraction, primer design and amplification of the RNA message and identification of the differentially expressed message was accomplished essentially as described above for the genes involved in picric acid degradation. The isolation of these genes demonstrates the applicability of the present method to gene isolation from consortia as opposed to pure cultures.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

Procedures required for PCR amplification, DNA modifications by endo-and exonucleases for generating desired ends for cloning of DNA, ligations, and bacterial transformation are well known in the art. Standard molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring, N.Y., 1984 and by Ausubel et al., *Current Protocols in Molecular Biology*; Greene Publishing and Wiley-Interscience; 1987.

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, DC, 1994 or by Brock, T. D.; *Biotechnology: A Textbook of Industrial Microbiology*, $2^{nd}$ ed.; Sinauer Associates: Sunderland, Mass., 1989. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified. Other materials were obtained from Qiagen, Valencia, Calif.; Roche Molecular Biochemicals, Indianapolis, Ind.; and Invitrogen, Carlsbad, Calif.

PCR reactions were run on GeneAMP PCR System 9700 using Amplitaq or Amplitaq Gold enzymes (PE Applied Biosystems, Foster City, Calif.). The cycling conditions and reactions were standardized according to manufacturer's instructions.

Precast polyacrylamide Excell gels and the "Plus-One" silver stain kit were from Amersham Pharmacia Biotech Piscataway, N.J.

| Plate #1 containing primers number A1 to A48 | | | | | | | | | | | |
|---|---|---|---|---|---|---|---|---|---|---|---|
| A1  | A1  | A2  | A2  | A3  | A3  | A4  | A4  | A5  | A5  | A6  | A6  |
| A7  | A7  | A8  | A8  | A9  | A9  | A10 | A10 | A11 | A11 | A12 | A12 |
| A13 | A13 | A14 | A14 | A15 | A15 | A16 | A16 | A17 | A17 | A18 | A18 |
| A19 | A19 | A20 | A20 | A21 | A21 | A22 | A22 | A23 | A23 | A24 | A24 |
| A25 | A25 | A26 | A26 | A27 | A27 | A28 | A28 | A29 | A29 | A30 | A30 |
| A31 | A31 | A32 | A32 | A33 | A33 | A34 | A34 | A35 | A35 | A36 | A36 |
| A37 | A37 | A38 | A38 | A39 | A39 | A40 | A40 | A41 | A41 | A42 | A42 |
| A43 | A43 | A44 | A44 | A45 | A45 | A46 | A46 | A47 | A47 | A48 | A48 |

Analysis of genetic sequences were performed with the sequence assembly program Sequencher (GeneCodes corp., Ann Arbor, Mich.). Sequence similarities were analyzed with the BLAST program at NCBI (Basic Local Alignment Search Tool; Altschul, S. F., et al., (1993) *J. Mol. Biol.* 215:403–410; see also www.ncbi.nlm.nih.gov/BLAST/). In any case where sequence analysis software program parameters were not prompted for, in these or any other program, default values were used, unless otherwise specified.

The meaning of abbreviations is as follows: "sec" means second(s), "min" means minute(s), "h" means hour(s), "d" means day(s), "$\mu$L" means microliter, "mL" means milliliters, "L" means liters, "mM" means millimolar, "M" means molar, "mmol" means millimole(s), "g" means gram, "$\mu$g" means microgram and "ng" means nanogram.

Bacterial Strains:

The bacterial strain used for these experiments is a derivative of *Rhodococcus erythropolis* HL 24-2 capable of degrading picric acid as well as dinitrophenol (Lenke et al., *Appl. Environ. Microbiol.* 58:2933–2937 (1992)).

R2A Medium:

Per liter: glucose 0.5 g, starch 0.5 g, sodium pyruvate 0.3 g, yeast extract 0.5 g, peptone 0.5 g, casein hydrolyzate 0.5 g, magnesium sulfate 0.024 g, potassium phosphate 0.3 g pH 7.2.

Minimal DNP Medium:

Per liter: 20 mM acetate, 54 mM $NaPO_4$ buffer pH 7.2 20 mg/L Fe(III)-citrate, 1 g/L $MgSO_4$ $7H_2O$, 50 mg/L $CaCl_2.2H_2O$ and 1 mL trace element solution (Bruhn et al., *Appl. Environ. Microbiol.* 53:208–210 (1987)).

Total RNA Extraction:

Cell disruption was performed mechanically in bead beater by zirconia/silica beads (Biospec Products, Bartlesville, Okla.) in the presence of a denaturant (i.e., acid phenol or Guanidinium Thiocyanate in the RNeasy kit). The total RNA was extracted using the RNeasy kit from Qiagen or with buffered water-saturated phenol at pH 5 and extracted successively with acid phenol, and a mixture of phenol/chloroform/isoamyl alcohol. Each RNA preparation is resuspended in 500 $\mu$L of DEPC treated $H_2O$, and treated with RNase-free DNase (Roche). Typically a 10 mL culture harvested at $A_{600nm}=1$ yields about 10–20 mg of cells wet weight that contain 400–800 ng of total RNA (assuming dry weight is 20% wet weight, RNA (stable+messenger RNA) is 20% of dry weight). The RNA extracted from a 10 mL culture is sufficient to perform the 240 RT-PCR reactions of a complete experiment.

Primer Design:

Primers were applied to 96 well plates as follows. The 240 primers are pre-aliquoted on five 96 well PCR plates. In each plate, 4 $\mu$L of each primer (2.5 $\mu$M) was placed in two adjacent positions as indicated below.

The ordering of the primers on the plates corresponded to the order of the systematic sequence variations in the design of the 3' end of the sequence CGGAGCAGATCGVVVVV (SEQ ID NO:22) (where VVVVV represents all the combinations of the three bases A, G and C at the last five positions of the 3' end). The following pattern was followed for each of the plates:

VVVVV was AAAAA in primer A1
VVVVV was AAAAC in primer A2
VVVVV was AAAAG in primer A3
VVVVV was AAACA in primer A4
VVVVV was AAACC in primer A5
VVVVV was AAACG in primer A6
VVVVV was AAAGA in primer A7
VVVVV was AAAGC in primer A8
VVVVV was AAAGG in primer A9
VVVVV was AACAA in primer A10 etc.

The algorithm of Breslauer et al. (*Proc. Natl. Acad. Sci. USA* 83:3746–3750 (1986)) was used to calculate the Tm of the primers in the collection. In this fashion the 240 primers were ranked by increasing Tm and separated into five 96-well plates, each corresponding to a narrower Tm interval.

RT-PCR Reactions:

The 480 RT-PCR reactions were performed in 96 well sealed reaction plates (PE Applied Biosystems, Foster City, Calif.) in a GeneAmp PCR System 9700 (PE Applied Biosystems, Foster City, Calif.). The enzyme used were the Ampli Taq DNA polymerase (PE Applied Biosystems, Foster City, Calif.) and the Plus One RT-PCR kit (Gibco BRL).

Separation and Visualization of PCR Products:

5 $\mu$L out each 25 $\mu$L RT-PCR reaction is analyzed on precast acrylamide gels (Excell gels Pharmacia Biotech). PCR products from control and induced RNA generated from the same primers are analyzed and compared.

Example 1

Induction of DNP Degradation Pathway by DNP

A culture of *Rhodococcus erythropolis* strain HL PM-1 grown overnight at 30° C. in minimal medium (20 mM acetate, 54 mM $NaPO_4$ buffer pH 7.2, 20 mg/L Fe(III)-citrate, 1 g/L $MgSO_4$ $7H_2O$, 50 mg/L $CaCl_2.2H_2O$ and 1 mL trace element solution (Bruhn et al., *Appl. Environ. Microbiol.* 53:208–210 (1987)) to an OD reading of 1.9 at 546 nm was diluted 20 fold in two 100 mL cultures, one of which received 0.55 mM dinitrophenol (DNP), the inducer of DNP and picric acid degradation. To characterize the induction of the DNP degradation pathway, cultures were then chilled on ice, harvested by centrifugation and washed three times with ice cold mineral medium. Cells were finally resuspended to an OD reading of 1.5 at 546 nm and kept on ice until assayed. 0.5 mL of each culture was placed in a water jacketed respirometry cell equipped with an oxygen electrode (Yellow Springs Instruments Co., Yellow Springs, Ohio) and with 5 mL of air saturated mineral medium at 30° C. After establishing the baseline respiration for each cell suspension, acetate or DNP was added to the final concentration of 0.55 mM and the rate of $O_2$ consumption was further monitored (FIG. 1). Control cells grown in the absence of DNP did not show an increase of respiration upon addition of DNP but did upon addition of acetate. In contrast cells exposed to DNP for 6 h increased their respiration upon addition of DNP indication. These results indicate that the picric acid degradation pathway is induced and the enzymes responsible for this degradation are expressed.

Example 2

Isolation of RNA from Control and Induced for PCR Reactions

Two 10 mL cultures of *Rhodococcus erythropolis* strain HM-PM1 were grown and induced as described in Example 1. Each culture was chilled rapidly in an ice/water bath and transferred to a 15 mL tube. Cells were collected by centrifugation for 2 min at 12,000×g in a rotor chilled to −4° C. The supernatants were discarded, the pellets resuspended in 0.7 mL of ice cold solution of 1% SDS and 100 mM sodium acetate at pH 5 and transferred to a 2 mL tube containing 0.7 mL of aqueous phenol (pH 5) and 0.3 mL of 0.5 mm zirconia beads (Biospec Products, Bartlesville, Okla.). The tubes were placed in a bead beater (Biospec Products, Bartlesville, Okla.) and disrupted at 2400 beats per min for two min.

Following the disruption of the cells, the liquid phases of the tubes were transferred to new microfuge tubes and the phases separated by centrifugation for 3 min at 15,000×g. The aqueous phase containing total RNA was extracted twice with phenol at pH 5 and twice with a mixture of phenol/chloroform/isoamyl alcohol (pH 7.5) until a precipitate was no longer visible at the phenol/water interface. Nucleic acids were recovered from the aqueous phase by ethanol precipitation with three volumes of ethanol, and the pellet resuspended in 0.5 mL of diethyl pyrocarbonate (DEPC) treated water. DNA was digested by 6 units of RNAse-free DNAse (Roche Molecular Biochemicals, Indianapolis, Ind.) for 1 h at 37° C. The total RNA solution was extracted twice with phenol/chloroform/isoamyl alcohol (pH 7.5), recovered by ethanol precipitation and resuspended in 1 mL of DEPC treated water to an approximate concentration of 0.2 mg per mL. The absence of DNA in the RNA preparation was verified in that ramdomly amplified PCR DNA fragments could not be generated by the Taq polymerase unless the reverse transcriptase was also present.

In other experiments, the cell pellets were resuspended in 0.3 mL of the chaotropic guanidium isothiocyanate buffer provided by the RNA extraction kit (Qiagen, Valencia, Calif.) and transferred in a separate 2 mL tube containing 0.3 mL of 0.5 mm zirconia beads (Biospec Products, Bartlesville, Okla.). The tubes were placed in a bead beater (Biospec Products, Bartlesville, Okla.) and disrupted at 2400 beats per min for two min. The total RNA was then extracted with the RNeasy kit from Qiagen. Each RNA preparation was then resuspended in 500 µL of DEPC treated $H_2O$ and treated with RNAse-free DNase (2U of DNase/100 µL RNA) for 1 h at 37° C. to remove DNA contamination.

Example 3

Performance of RT-PCR using 240 Oligonucleotide Fragments

The complete RT-PCR experiment of 480 reactions (240 primers tested on two RNA preparations) were performed in five 96-well format, each containing 5 µL of 2.5 µM of 48 arbitrary primers prealiquoted as described above. A RT-PCR reaction master mix based on the RT-PCR kit "Superscript One-Step RT-PCR System" (Gibco/BRL Gaithersburg, Md.) was prepared on ice as follows:

|  | Per 25 µL reaction | Per 96 + 8 reactions |
| --- | --- | --- |
| 2X reaction mix | 12.5 µL | 1300 µL |
| $H_2O$ | 6.0 µL | 624 µL |
| RT/Taq | 0.5 µL | 52 µL |
| Total | 19.0 µL | 1976 µL |

The master mix was split in two tubes receiving 988 µL each. Fifty-two µL of total RNA (20–100 ng/µL) from the control culture was added to one of the tubes and 52 µL of total RNA (20–100 ng/µL) from the induced culture were added to the other tube. Using a multipipetter, 20 µL of the reaction mix containing the control RNA template were added to the tubes in the odd number columns of the 96 well PCR plate and 24 µL of the reaction mix containing the "induced" RNA template were added to the tubes in the even number columns of the 96 well PCR plate, each plate containing 5 µl of prealiquoted primers. All manipulations were performed on ice. Heat denaturation of the RNA to remove RNA secondary structure prior to the addition of the reverse transcriptase was omitted in order to bias against the annealing of the arbitrary primers to the stably folded ribosomal RNAs.

The PCR machine was programmed as follows: 4° C. for 2 min; ramp from 4° C. to 37° C. for 5 min; hold at 37° C. for 1 h; 95° C. for 3 min, 1 cycle; 94° C. for 1 min, 40° C. for 5 min, 72° C. for 5 min, 1 cycle; 94° C. for 1 min, 60° C. for 1 min, 72° C. for 1 min, 40 cycles; 72° C. for 5 min, 1 cycle; hold at 4° C. To initiate the reaction, the PCR plate was transferred from the ice to the PCR machine when the block was at 4° C.

Example 4

Electrophoresis Analysis and Visualization of PCR Products and Identification of Differentially Expressed Bands 240 pairs of RT-PCR reactions were primed by the collection of 240 oligonucleotides (as described above). Pairs of RT-PCR reaction (corresponding to an RT-PCR sampling of the mRNA from control and induced cells) were analyzed on 10 precast acrylamide gels, 48 lanes per gels (Excell gels, Amersham Pharmacia Biotech, Piscataway, N.J.). PCR products from control and induced RNA generated from the same primers were analyzed side by side. The PCR fragments were visualized by staining gels with the "Plus One" DNA silver staining Kit (Amersham Pharmacia Biotech, Piscataway, N.J.), shown in FIG. 2. In this manner, a series of 240 RT-PCR reactions were performed for each RNA sample. On average each RT-PCR reaction yielded ~20 clearly visible DNA bands (FIG. 2) leading to a total number of bands about 5000. RAPD Patterns generated from the RNA of control and DNP-induced cells using the same primer are extremely similar. Examples of differentially amplified bands are identified with an arrow in FIG. 2.

Example 5

Elution and Reamplification of the DNA RT-PCR Band

Of the bands visualized in Example 4, 48 differentially amplified DNA fragment bands were excised from the silver stained gel with a razor blade and placed in a tube containing 25 μL of elution buffer: 20 mM NaCN, 20 mM Tris-HCl pH 8, 50 mM KCl, 0.05% NP40 and heated to 95° C. for 20 min to allow some of DNA to diffuse out of the gel. The eluate solution was used in a PCR reaction and consisted of: 5 μL 10×PCR buffer, 5 μL band elution supernatant, 5 μL 2.5 μM primer, 5 μL dNTPs at 0.25 mM, 30 μL water and 5 μL Taq polymerase.

When the reamplification used the arbitrary primer that had generated the RAPD pattern ("specific primer"), the PCR machine was programmed as follows: 94° C. for 5 min; 94° C. for 1 min; 55° C. for 1 min; 72° C. for 1 min for 20 cycles, 72° C. for 7 min hold; 4° C. hold. When the cyanide was not incorporated in the elution buffer, the reamplification of the band often needed more PCR cycles.

In other experiments when the reamplification used the universal reamplification primer (5'-AGTCCACGGAGCATATCG-3' (SEQ ID NO:23) was used, the PCR machine was programmed as follows: 94° C. for 5 min; 94° C. for 30 sec; 40° C. for 1 min; ramp to 72° C. in 5 min; 72° C. for 5 min for 5 cycles; 94° C. for 1 min, 55° C. for 1 min; 72° C. for 1 min for 40 cycles; 72° C. for 5 min, hold at 4° C.

Analysis of the reamplified fragments was performed on 1% agarose gel stained with ethidium bromide as shown for three different fragments in FIG. 3. The reamplification of a differentially amplified band eluted from the polyacrylamide gel yielded the same PCR fragment with both reamplification primer. As shown in FIG. 3, DNA fragments reamplified with the universal primer (noted U) are slightly longer than those reamplified with the specific primer (noted S) because they include 8 additional bases at each end present in the universal reamplification primer. The lane labeled "M" indicates the molecular weight marker.

Example 6

Cloning, Sequencing and Contig Assembly of the Differentially Expressed DNA Fragments 48 RAPD fragments differentially amplified in the RT-PCR reactions from "induced" samples but not in the control RT-PCR reactions were identified and reamplified as described in Experiment 5. The product of each reamplification was cloned in the vector pCR2.1 (Invitrogen) and eight clones were isolated from the cloning of each reamplified band. The nucleotide sequence of each insert was determined, trimmed for vector, primer and low quality sequences and aligned with the alignment program, "Sequencher" (Gene Code Corp., Ann Arbor, Mich.) and assembled into contigs. The assembly parameters were 80% identity over 50 bases. The number of sequences comprised in each contig were plotted (FIG. 4) and the nucleotide sequence of the contigs assembled from DNA fragments generated in independent RT-PCR reactions was then compared to nucleic acid and amino acid sequences in the GenBank database.

Several contigs were assembled from the sequence of DNA bands generated in several independent RT-PCR reactions. These contigs, named according to that of homologous sequences, are listed in Table 1.

TABLE 1

Homologies of contigs assembled from more than one band and more than one primer

| Best homology | Multiplicity of Sampling Size | Contig |
| --- | --- | --- |
| F420-dependent Dehydrogenase | 6 Primers/9 Bands | 1.7 kb |
| Aldehyde Dehydrogenase | 4 Primers/4 Bands | 0.7 kb |
| F420-dependent Oxidoreductase | 4 Primers/4 Bands | 1.1 kb |
| RNA Polymerase α Subunit | 4 Primers/4 Bands | 1.1 kb |
| 16S RrnA | 4 Primers/4 Bands | 1.1 kb |
| 23S rRNA | 4 Primers/4 Bands | 1.2 kb |
| ATP Synthase | 3 Primers/3 Bands | 0.9 kb |
| Transcriptional Regulator | 2 Primers/4 Bands | 0.8 kb |
| Transcription Factor | 2 Primers/2 Bands | 0.7 kb |

Among these contigs, two showed homology to F420-dependent enzymes suggesting the involvement of Factor F420 in the degradation of the picric acid. The complete sequence of a F420-dependent dehydrogenase (FIG. 6, ORF3) was generated directly by the overlap of the sequence of differentially amplified bands which allowed the synthesis of PCR primers for the direct cloning of this gene. The partial sequence of a second F420-dependent gene encoding an F420/NADPH oxidoreductase was also identified.

Oligonucleotide primers corresponding to the ends of the F420-dependent Dehydrogenase gene (FIG. 6, ORF3) were next used to identify two clones from a large (>10) insert plasmid library that carried that gene. The subsequent sequencing of these clones showed that four of the contigs identified (Table 1) were linked to a single gene cluster (FIG. 6). This 12 kb sequence was sampled 21 times out of the 48 differentially expressed bands identified. Within that sequence, a third gene (FIG. 6, ORF8), the 3' end sequence (180 bp) of which had been sampled by differential display, encoding for an F420-dependent dehydrogenase was identified on the basis of sequence similarities. The 12 kb gene cluster encodes for 10 genes. The beginning and the end of the genes were determined by comparison with homologous sequences. Where possible, an initiation codon (ATG, GTG, or TTG) was chosen which was preceded by an upstream ribosome binding site sequence (optimally 5–13 bp before the initiation codon). If this could not be identified the most upstream initiation codon was used. The best homologies to each ORF, and thus their putative function in the degradation pathway of picric acid are listed in Table 2. Finally, a contig assembled from the sequences corresponding to the cloning of a single differentially amplified DNA fragment matched the sequence of ORF10 (acyl-CoA dehydrogenase).

TABLE 2

| ORF | Similarity Identified | SEQ ID Nucl. | SEQ ID Peptide | % Identity[a] | % Similarity[b] | E-value[c] | Citation |
|---|---|---|---|---|---|---|---|
| 1 | sp\|Q10550\|YZ18_MYCTU Putative regulatory protein CY31.18C [*Mycobacterium tuberculosis*] | 2 | 3 | 32% | 45% | 3e-25 | Murphy, et al. direct submission May 1996 |
| 2 | (AE001036) L-carnitine dehydratase [*Archaeoglobus fulgidus*] | 4 | 5 | 34% | 52% | 9e-51 | Klenk, H. P. et al. Nature 390 (6658), 364–370 (1997) |
| 3 | >pir\|E64491 N5,N10-methylene tetrahydromethanopterin reductase [*Methanococcus jannaschii*] | 6 | 7 | 24% | 42% | 6e-12 | Bult, C. J. et al. Science 273 (5278), 1058–1073 (1996) |
| 4 | (U24215) p-cumic aldehyde dehydrogenase [*Pseudomonas putida*] | 8 | 9 | 44% | 60% | 2e-99 | Eaton, R. W. J. Bacteriol. 178 (5), 1351–1362 (1996) |
| 5 | >sp\|P39062\| Acetate CoA ligase [*Bacillus subtilis*] | 10 | 11 | 27% | 42% | 5e-42 | Grundy, F. J. et al. Mol. Microbiol. 10:259–271 (1993) |
| 6 | (AE000277) Transcriptional Regulator Kdgr [*Escherichia coli*] | 12 | 13 | 26% | 42% | 3e-11 | Blattner, F. R., et al. RL SCIENCE 277:1453–1474 (1997). |
| 7 | >sp\|O26350\| F420-Dependent NADP Reductase (AE000811) [*Methanobacterium thermoautotrophicum*] | 14 | 15 | 32% | 44% | 1e-18 | Smith, D. R. et al. J. Bacteriol. 179:7135–7155 (1997) |
| 8 | >gi\|2649522 (AE001029) N5,N10-Methylenetetrahydromethanopterin Reductase [*Archaeoglobus fulgidus*] | 16 | 17 | 28% | 46% | 7e-26 | Klenk, H. P. et al. Nature 390 (6658), 364–370 (1997) |
| 9 | >gi\|97441\|pir\|S19026 Enoyl-CoA Hydratase [*Rhodobacter capsulatus*] | 18 | 19 | 26% | 38% | 9e-08 | Beckman D. L et al.; Gene 107:171–172 (1991). |
| 10 | gi\|2649289 (AE001015) acyl-CoA dehydrogenase (acd-9) [*Archaeoglobus fulgidus*] | 20 | 21 | 32% | 54% | 5e-44 | Klenk, H. P. et al. Nature 390 (6658), 364–370 (1997) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 7

Cloning and Expression of Two F420-dependent Genes Involved in the Degradation of Picric Acid To confirm that the gene cluster identified by differential display was indeed involved in the degradation of nitrophenols, the gene for two F420-dependent enzymes were cloned and expressed in *E. coli*. ORF7 was shown to encode an F420/NADPH oxido-reductase. FIG. 7 shows the spectral changes of a solution of NADPH (0.075 mM) and F420 (0.0025 mM) in 50 mM sodium citrate buffer (pH 5.5) upon addition of cell extracts of *E. coli* expressing the F420/NADPH oxidoreductase (ORF 7). The characteristic disappearance of absorbance peaks at 400 and 420 nM corresponds to the reduction of factor F420. The activity of the enzyme encoded by ORF 8 was shown spectrophotometrically in a cuvette containing NADPH (0.075 mM), F420 (0.0025 mM) DNP or picric acid (0.025 mM) and *E. coli* extracts expressing the F420/NADPH oxidoreductase (ORF 7). The F420/NADPH oxidoreductase was added as a reagent to reduce F420 with NADPH. Upon addition of *E. coli* extracts expressing the F420-dependent dehydrogenase (ORF 8), reduced F420 reduces picric acid (FIG. 8A) or dinitrophenol (FIG. 8B). The spectral changes match those reported for the formation of the respective Meisenheimer complexes of picric acid and dinitrophenol (Behrend et al., Appl. Environ. Microbiol. 65:1372–1377 (1999)), thus confirming that ORF8 encodes for the F420-dependent picric/dinitrophenol reductase.

Example 8

Identification of Genes Involved in Cyclohexanone Oxidation by Differential Display Analysis of an Enrichment Culture An enrichment culture growing at 30° C. on cyclohexanone as a sole carbon source was started with sludge from a wastewater plant. The population was analyzed by Terminal Restriction Fragment Length Polymorphism (TRFPL) of 16S rDNA amplified using universal primers and analyzed by an ABI (Liu et al., Appl. Envir. Microbiol. 63:4516–4522 (1997)). It was shown to be composed of 37% Arthrobacter sp. and two distinct Rhodococcus species accounting for 25% and 23% of the cells respectively. Seven other species accounted for the remaining 15% of the cells. The inducibility of the cyclohexanone oxidation pathway in the bacterial population was demonstrated by respirometry as in Example 1.

The enrichment culture was washed in 10 mL mineral medium and grown overnight in 0.1% R2A medium. After 14 h, the culture was split and one half received 0.1% cyclohexanone, whereas the other half remained as the control. Cells were further incubated at 30° C. for 3 h and RNA was extracted as described in Example 2. High density RT-PCR reactions were performed on the RNA samples as described in Example 3. The RT-PCR DNA fragments were analyzed by polyacrylamide gel electrophoresis as described in Example 4. Differentially amplified DNA fragments were excised from the gels and reamplified as described in Example 5 and cloned and sequenced as described in Example 6. Contigs were assembled and the nucleic acid sequences were compared to protein sequence databases.

Thirteen differentially expressed DNA fragments showed strong similarity to cyclohexanone degradation genes identified elsewhere (Table 3). In particular several gene fragments encoding for a cyclohexanone monooxygenase showed 45–67% homology to the Acinetobacter gene. Analysis of the codon usage of these partial genes sequences suggest that they belong to a high G+C organism of the Rhodococcus or Arthrobacter group. Other gene fragments had sequence similarity to a caprolactone esterase, an alcohol dehydrogenase, an hexanoate semi-aldehyde dehydrogenase genes involved, or part of gene clusters including a transcriptional regulator involved, in the degradation of cyclo-alkanones or present on by Acinetobacter and Brevibacterium species confirming that these genes fragments correspond to the pathway targeted by the by high density differential display experiment. These results demonstrate the feasibility of identifying microbial metabolic genes not only in pure cultures but also in enrichment cultures containing several microbial species.

TABLE 3

Similarity of Genes

| SEQ ID NO | Sequence | Similarity Identified | % Identity |
|---|---|---|---|
| SEQ ID NO:25 | GADRTKAITMTAQISP TVVDAVVIGAGFADLRR AQAAQRTGPDRGRFRQG GRPRRYLVLEPLPGGALR HRESSLPLLVRSAP | >pir\|A28550 cyclohexanone monooxygenase (EC 1.14.13.22)- Acinetobacter sp | 65% |
| SEQ ID NO:26 | EQIETQVEWISDTVAY AERNEIRAIEPTPEAEEE WTQTCTDIANATLFTRG DSWIFGANVPGKKPSVLF YLGGLGNYRNVLAGVV ADSYRGFELK | (AB006902) cyclohexanone 1,2-monooxygenase [Acinetobacter sp.] | 58% |
| SEQ ID NO:27 | ATLFTKGDSWIFGANIPG KTPSVLFYLGGLRNYRA VLAEVATDGYRGFDVK | (AB006902) cyclohexanone 1,2-monooxygenase [Acinetobacter sp.] | 60% |
| SEQ ID NO:28 | IETQVEWISDTVPTPSA TRSVRSNPPRSRGGVDA DLHRHREPTLFTRGDSWI FGANVPGKKPSVLFYLG LGNYRNVLAGVVADS YRGFELK | (AB006902) cyclohexanone 1,2-monooxygenase [Acinetobacter sp.] | 45% |
| SEQ ID NO:29 | EWISDTIGYAERNGVRAI EPTPEAEARMDRDLHRD RDATLFTKGDSWIFGANI PGKTPSVLFYLGGLRNY RAVLAEVATDGYRGFDV K | (AB006902) cyclohexanone 1,2-monooxygenase [Acinetobacter sp.] | 52% |
| SEQ ID NO:30 | PMGVYTTIDPATGDATA QYPKISDAELDTLIKNSA AAYRSWRTTTLEQRRAV LTRTASI | (AB003475) succinic semialdehyde dehydrogenase [Deinococcus radiodurans] | 30% |
| SEQ ID NO:31 | DQSKVLLYTHGGGFAVG SPPSHRKLAAHVAKALG SVSFVLDYRAPPNSSTRH RSKTWPPSMPSSPASPLR TSPPSVIPGGNLAIAIALD LL | >Pir\|\|PT0060 N-acetylphosphino- thricin-tripetide- deacetylase - Streptomyces viridochromogenes | 44% |
| | | >Brevibacteriurn sp. HCU esterase (BC-1001) | 56% |
| SEQ ID NO:32 | KHTYITQPEILEYLEDVV DRFDLRRTFRFGTEVKSA TYLEDEGLWEVTTGGGA VYRAKYVINAVGLLSAI NFP | (AB006902) cyclohexanone 1,2-monooxygenase [Acinetobacter sp.] | 45% |
| SEQ ID NO:33 | RGVEELDELVQGRSSH GAKLLLGGERPDGPAY YPATVLAGVTPAMRAFT EELFGPVAVVYRVGSLQ EAIDL | (AB006902) cyclohexanone 1,2-monooxygenase [Acinetobacter sp.] | 51% |

TABLE 3-continued

Similarity of Genes

| SEQ ID NO | Sequence | Similarity Identified | % Identity |
|---|---|---|---|
| SEQ ID NO:34 | AEEEWTQTCTDIAEPTLF TRGDSWIFGANVPGKKP SVLFYPGGLGNYRNVLA | (AB006902) cyclohexanone 1,2-monooxygenase [Acinetobacter sp.] | 67% |
| SEQ ID NO:35 | IAESGFGSLTIEGVAERSG VAKTTIYRRHRSRNDLA LAVLLDMVGDVSTQP | (AL118515) probable tetR family transcriptional regulator [Streptomyces coelicolor A3(2)] | 45% |
| SEQ ID NO:36 | ARTERAVMDAARELLAE SGFGSLTIEGVAERSGVA KTTIYR | (AL133220) putative TetR-family transcriptional regulator [Streptomyces coelicolor A3(2)] | 56% |
| SEQ ID NO:37 | QIAEIIEDPETARKLMPTG LYAKRPLCDNGYYEVYN RPNVEAVAIKENPIRE | >gi\|141768 (M19029) cyclohexanone monooxygenase [Acinetobacter sp.] | 61% |

What is claimed is:

1. A method for the identification of differentially expressed genes comprising:
   (i) separating a first and second population of microbial cells, wherein the first population of cells is contacted with a stimulating agent;
   (ii) extracting total RNA from the first and second population of microbial cells of step (i);
   (iii) amplifying the extracted RNA of the first and second populations of microbial cells by a process comprising:
      a) preparing a collection of at least 32 different arbitrary primers, each primer comprising a common region and a variable region;
      b) individually contacting each different primer of step (a) with a sample of the extracted RNA from the first and second population of microbial cells under conditions wherein a set of first and second amplification products are produced;
   (iv) purifying the first and second amplification products of step (iii);
   (v) identifying the amplification products generated from the first population of microbial cells that differ from the amplification products generated from the second population of microbial cells as differentially expressed genes; and
   (vi) optionally sequencing the identified differentially expressed genes of step (v).

2. A method according to claim 1 wherein said population of microbial cells is selected from the group consisting of bacteria, archaebacteria, yeasts and filamentous fungi.

3. A method according to claim 1 wherein said stimulating agent is selected from the group consisting of chemicals, environmental pollutants, changes in temperature, changes in pH, agents producing oxidative damage, agents producing DNA damage, anaerobiosis, and pathogenesis.

4. A method according to claim 1 wherein said collection of arbitrary primers contains from about 80 to 500 primers.

5. A method according to claim 4 wherein said collection of arbitrary primers contains from about 100 to 250 primers.

6. A method according to claim 1 wherein said common region of said arbitrary primer is from about 10 bases to about 20 bases in length.

7. A method according to claim 1 wherein said variable region of said arbitrary primer is from about 4 to about 8 bases in length.

8. A method according to claim 1 wherein within the collection of primers, no two primers are identical.

9. A method according to claim 1 wherein the conditions where a set of first and second amplification products are produced employ low stringency amplification protocols.

10. A method according to claim 9 wherein the annealing temperature of the low stringency conditions is from about 30° C. to about 40° C.

11. A method according to claim 1 wherein the population of cells is a pure culture.

12. A method according to claim 1 wherein the population of cells is a consortium.

13. A method according to claim 1 wherein after the sequencing step (iv) the differential genes are assembled into large contiguous sequences by computational means or genetic means.

14. A method for distinguishing genetic differences between two populations of cells comprising:
   (i) separating a first and second population of microbial cells, wherein the first population of cells and second population of cells differ in genotype;
   (ii) extracting total RNA from the first and second population of microbial cells of step (i);
   (iii) amplifying the extracted RNA of the first and second populations of microbial cells by a process comprising:
      a) preparing a collection of at least 32 different arbitrary primers, each primer comprising a common region and a variable region;
      b) individually contacting each different primer of step (a) with a sample of the extracted RNA from the first and second population of microbial cells under conditions where a set of first and second amplification products are produced;
   (iv) purifying the first and second amplification products of step (iii);
   (v) identifying the amplification products generated from the first population of microbial cells that differ from the amplification products generated from the second population of microbial cells; and
   (vi) optionally sequencing the identified genes of step (v).

15. A method according to claim 14 wherein said population of microbial cells is selected from the group consisting of bacteria, archaebacteria, yeasts and filamentous fungi.

16. A method according to claim 14 wherein said collection of arbitrary primers contains from about 80 to 500 primers.

17. A method according to claim 16 wherein said collection of arbitrary primers contains from about 100 to 250 primers.

18. A method according to claim 14 wherein said common region of said arbitrary primer is from about 10 bases to about 20 bases in length.

19. A method according to claim 14 wherein said variable region of said arbitrary primer is from about 4 to about 8 bases in length.

20. A method according to claim 14 wherein within the collection of primers, no two primers are identical.

21. A method according to claim 14 wherein the conditions where a set of first and second amplification products are produced employ low stringency amplification protocols.

22. A method according to claim 14 wherein the population of cells is a pure culture.

23. A method according to claim 14 wherein the population of cells is a consortium.

24. A DNA fragment as set forth in SEQ ID NO:22, consisting of the sequence 5'-CGGAGCAGATCGVVVVV-3' wherein each V may be independently selected from the group of bases consisting of A, G, and C.

25. A method for the identification of differentially expressed genes comprising:
 (i) separating a first and second population of bacterial cells, wherein the first population of cells is contacted with a stimulating agent;
 (ii) extracting total RNA from the first and second population of bacterial cells of step (i);
 (iii) amplifying the extracted RNA of the first and second populations of bacterial cells by a process comprising:
  a) preparing a collection of from about 80 to about 500 different arbitrary primers, each primer comprising a common region and a variable region;
  b) individually contacting each different primer of step (a) with a sample of the extracted RNA from the first and second population of bacterial cells under conditions where a set of first and second amplification products are produced;
 (iv) purifying the first and second amplification products of step (iii);
 (v) identifying the amplification products generated from the first population of bacterial cells that differ from the amplification products generated from the second population of bacterial cells as differentially expressed genes; and
 (vi) optionally sequencing the identified differentially expressed genes of step (v).

26. A method for distinguishing genetic differences between two populations of bacterial cells comprising:
 (i) separating a first and second population of bacterial cells, where the first population of cells and second populations of cells differ in genotype;
 (ii) extracting total RNA from the first and second population of bacterial cells of step (i);
 (iii) amplifying the extracted RNA of the first and second populations of bacterial cells by a process comprising:
  a) preparing a collection of at from about 80 to about 500 different arbitrary primers, each primer comprising a common region and a variable region;
  b) individually contacting each different primer of step (a) with a sample of the extracted RNA from the first and second population of bacterial cells under conditions where a set of first and second amplification products are produced;
 (iv) purifying the first and second amplification products of step (iii);
 (v) identifying the amplification products generated from the first population of bacterial cells that differ from the amplification products generated from the second population of bacterial cells; and
 (vi) optionally sequencing the identified genes of step (v).

\* \* \* \* \*